US011766456B2

(12) United States Patent
Min et al.

(10) Patent No.: US 11,766,456 B2
(45) Date of Patent: Sep. 26, 2023

(54) METHOD FOR CULTURING NATURAL KILLER CELLS USING T CELLS

(71) Applicants: GC CELL CORPORATION, Yongin-si (KR); Mogam Institute for Biomedical Research, Yongin-si (KR)

(72) Inventors: Bo Kyung Min, Yongin-si (KR); Hana Choi, Yongin-si (KR); Yu Kyeong Hwang, Yongin-si (KR)

(73) Assignees: GC Cell Corporation; Mogam Institute for Biomedical Research

( * ) Notice: Subject to any disclaimer, the term of this patent is extended or adjusted under 35 U.S.C. 154(b) by 0 days.

(21) Appl. No.: 17/220,865

(22) Filed: Apr. 1, 2021

(65) Prior Publication Data

US 2021/0268025 A1    Sep. 2, 2021

Related U.S. Application Data

(63) Continuation of application No. 15/527,752, filed as application No. PCT/KR2015/012700 on Nov. 25, 2015, now abandoned.

(30) Foreign Application Priority Data

Nov. 26, 2014   (KR) .................. 10-2014-0166705

(51) Int. Cl.
| | | |
|---|---|---|
| *A61K 35/17* | (2015.01) | |
| *C12N 5/0783* | (2010.01) | |
| *C12N 5/00* | (2006.01) | |
| C07K 14/55 | (2006.01) | |
| C12N 5/09 | (2010.01) | |
| A61K 35/12 | (2015.01) | |

(52) U.S. Cl.
CPC ............ *A61K 35/17* (2013.01); *C12N 5/0646* (2013.01); *A61K 2035/124* (2013.01); *C12N 2501/2302* (2013.01); *C12N 2501/515* (2013.01); *C12N 2502/1114* (2013.01)

(58) Field of Classification Search
None
See application file for complete search history.

(56) References Cited

U.S. PATENT DOCUMENTS

| | | |
|---|---|---|
| 5,882,650 A | 3/1999 | Ennis |
| 9,062,287 B2 | 6/2015 | Ideno et al. |
| 9,834,753 B2 | 12/2017 | Min et al. |
| 2003/0068306 A1 | 4/2003 | Dilber |
| 2007/0048290 A1 | 3/2007 | Tsai |
| 2008/0138833 A1 | 6/2008 | Braun et al. |
| 2010/0178276 A1 | 7/2010 | Sadelain et al. |
| 2012/0045423 A1 | 2/2012 | Har-Noy |
| 2013/0011376 A1 | 1/2013 | Peled et al. |
| 2014/0050710 A1 | 2/2014 | Gonzalez et al. |
| 2014/0080148 A1 | 3/2014 | Spanholtz |
| 2015/0152387 A1 | 6/2015 | Lee et al. |
| 2017/0319621 A1 | 11/2017 | Min et al. |
| 2019/0037831 A1 | 2/2019 | Hwang et al. |
| 2019/0336533 A1 | 11/2019 | Hwang et al. |
| 2020/0108096 A1 | 4/2020 | Min et al. |
| 2021/0147803 A1 | 5/2021 | Hwang et al. |
| 2021/0179733 A1 | 6/2021 | Lee et al. |

FOREIGN PATENT DOCUMENTS

| | | |
|---|---|---|
| CN | 103068973 | 4/2013 |
| CN | 102112600 | 9/2014 |
| CN | 102911918 | 12/2014 |
| CN | 106222141 | 12/2016 |
| EP | 2856876 | 4/2015 |
| EP | 3633029 | 4/2020 |
| JP | 2004-501110 | 1/2004 |
| JP | 2008-544760 | 12/2008 |
| JP | 2010-501173 | 1/2010 |
| JP | 2010-523083 | 7/2010 |
| JP | 2011-529341 | 12/2011 |
| JP | 2012-521215 | 9/2012 |
| JP | 2013-006793 | 1/2013 |
| JP | 2013-027385 | 2/2013 |
| JP | 2013-071915 | 4/2013 |
| JP | 2015-502756 | 1/2015 |
| JP | 2015-513403 | 5/2015 |
| JP | 2018-520993 | 8/2015 |
| JP | 5840837 | 1/2016 |

(Continued)

OTHER PUBLICATIONS

Edwards et al (JMB, 2003, 334:103-118) (Year: 2003).*
Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) (Year: 2014).*
Poosarla et al (Biotechn. Bioeng., 2017, 114(6): 1331-1342) (Year: 2017).*
Torres and Casadevall (Trend. Immunol., 2008, 29(2): 91-97) (Year: 2008).*
Freshney, R.l. (Culture of Animal Cells, A Manual of Basic Technique, Alan R. Liss, Inc., 1983, New York, p. 4) (Year: 1983).*
Dermer, G (Bio/Technology, 1994, 12:320) (Year: 1994).*
Zips et al (In Vivo, 2005, 19:1-7) (Year: 2005).*

(Continued)

*Primary Examiner* — G. R. Ewoldt
*Assistant Examiner* — Marianne DiBrino
(74) *Attorney, Agent, or Firm* — Fish & Richardson P.C.

(57) ABSTRACT

The present invention relates to a method for producing natural killer cells using T cells, and more particularly, to a method for producing natural killer cells, which comprises culturing seed cells using CD4(+) T cells as feeder cells. The method for producing natural killer cells using T cells according to the present invention is a method capable of producing natural killer cells by selectively proliferating only natural killer cells from a small amount of seed cells while maintaining the high killing activity of the natural killer cells. The method of the present invention can produce a large amount of natural killer cells that can be frozen, and thus is useful for commercialization of cell therapeutic agents.

14 Claims, 11 Drawing Sheets

(56) References Cited

FOREIGN PATENT DOCUMENTS

| | | |
|---|---|---|
| JP | 2017-525370 | 9/2017 |
| JP | 2018-501779 | 1/2018 |
| JP | 7039623 | 3/2022 |
| KR | 10-2008-0008060 | 1/2008 |
| KR | 10-2009-0121694 | 11/2009 |
| KR | 10-2010-0011586 | 2/2010 |
| KR | 10-2010-0012586 | 2/2010 |
| KR | 10-1035556 | 5/2011 |
| KR | 10-1133185 | 5/2011 |
| KR | 10-2011-0132618 | 12/2011 |
| KR | 10-2012-0091012 | 8/2012 |
| KR | 10-1298012 | 8/2013 |
| KR | 10-2014-0123503 | 10/2014 |
| KR | 10-1520534 | 5/2015 |
| KR | 10-2016-0063114 | 6/2016 |
| KR | 10-2016-0066837 | 6/2016 |
| KR | 10-1644984 | 8/2016 |
| KR | 10-1706524 | 2/2017 |
| WO | WO 1997/005239 | 2/1997 |
| WO | WO 1997/032970 | 9/1997 |
| WO | WO 19980/06822 | 2/1998 |
| WO | WO 2005/007116 | 12/2006 |
| WO | WO 2007/111677 | 10/2007 |
| WO | WO 2008/023874 | 2/2008 |
| WO | WO 2008/121420 | 10/2008 |
| WO | WO 2008/133845 | 11/2008 |
| WO | WO 2008/138214 | 11/2008 |
| WO | WO 2009/060865 | 5/2009 |
| WO | WO 2009/132192 | 10/2009 |
| WO | WO 2009/151183 | 12/2009 |
| WO | WO 2010/013947 | 5/2010 |
| WO | WO 2010/110734 | 9/2010 |
| WO | WO 2011/080740 | 7/2011 |
| WO | WO 2013/094988 | 6/2013 |
| WO | WO 2014/188680 | 11/2014 |
| WO | WO 2015/157386 | 10/2015 |
| WO | WO 2016/085248 | 6/2016 |
| WO | WO 2016/139463 | 9/2016 |
| WO | WO 2017/135631 | 8/2017 |
| WO | WO 2018/124766 | 7/2018 |
| WO | WO 2018/197859 | 11/2018 |
| WO | WO 2018/217064 | 11/2018 |
| WO | WO 2019/098682 | 5/2019 |
| WO | WO 2019/182392 | 9/2019 |
| WO | WO 2020/101361 | 5/2020 |
| WO | WO 2022/133057 | 6/2022 |

OTHER PUBLICATIONS

Vitale et al (Eur. J. Immunol. 2014, 44: 1582-1592) (Year: 2014).*
Holmes et al (J. Immunol. 2011, 186: 1538-1545) (Year: 2011).*
Dahlberg et al (Front. Immunol. 2015, 6: pp. 1-19) (Year: 2015).*
Byers, T (Cancer Journal, 1999, 49: 353-361) (Year: 1999).*
Childs and Berg (Hematol Am Soc Hematol Educ Program, 2013, 1: 234-246) (Year: 2013).*
Miyahira, A (Sanguine Bio Researcher 2012, pp. 1/3-3/3, technical.sanguinebio.com/types-of-immune-cells-present-in-human-pbmc/) (Year: 2012).*
Lim et al (PLoS ONE, published Jan. 11, 2013, 8(1): e53611, pp. 1-9) (Year: 2013).*
Sieglier et al (Cytotherapy, 2010, 12: 750-763) (Year: 2010).*
Denman et al (PLoS ONE, Jan. 18, 2012, 7(1): e30264, pp. 1-13) (Year: 2012).*
Millipore Sigma (2021) (Year: 2021).*
Biology Online Dictionary (2021), 3 pages (Year: 2021).*
Cell-line meaning (2021), 3 pages (Year: 2021).*
Min et al (Cell. Molec. Immunol. 2022 19: 296-298, Supplemental Figure S4 only) (Year: 2022).*
Valle et al (J. Immunol. 2015, 194: 2117-2127) (Year: 2015).*
Ando et al., "Extensive generation of human cord blood CD34 stem cells from Lin 2CD34 cells in a long-term in vitro system" Exp, Hematol., 2000 28:690-9.

AU Office Action in Australian Appln. No. 2015354941, dated Jun. 29, 2018, 7 pages.
Bae et al., "Development of NK cell expansion methods using feeder cells from human myelogenous leukemia cell line," Blood Research, Sep. 2014, 49(3):154-61.
Baek et al., "Ex Vivo Expansion of Natural Killer Cells Using Cryopreserved Irradiated Feeder Cells," Anticancer Res., Jan. 2013, 33:2011-2020.
Berg et al., ""Clinical Grade Ex Vivo-Expanded Human Natural Killer Cells Upregulate Activating Receptors and Death Receptor Ligands and Have Enhanced Cytolytic Activity against Tumor Cells,"" Cytotherapy, 2009, 11(3):41-355.
Boissel et al., "Umbilical Cord Mesenchymal Stem Cells Increase Expansion of Cord Blood Natural Killer Cells," Biology of Blood and Marrow Transplantation, Sep. 2008, 14(9):1031-8.
Carlens et al., "A New Method for In Vitro Expansion of Cytotoxic Human CD3-CD56+ Natural Killer Cells," Human Immunology, Oct. 2001, 62(10):1092-8.
Castriconi et al., "Human NK cell infusions prolong survival of metastatic human neuroblastoma-bearing NOD/scid mice" Cancer Immunol. Immunother., Nov. 2007, 56(11):1733-42.
CN Office Action in Chinese Application No. 201580063858.5, dated Jul. 21, 2020, 10 pages (with English Translation).
CN Office Action in Chinese Application No. 201580063858.5, dated Nov. 28, 2019, 12 pages (with English Translation).
Condiotti et al., "Ex vivo expansion of CD56+ cytotoxic cells from human umbilical cord blood," Experimental Hematol., 2001, 29(1):104-13.
Dewan et al., "Role of natural killer cells in hormone-independent rapid tumor formation and spontaneous metastasis of breast cancer cells in vivo" Breast Cancer Res. Treatment, 2007, 104(3):267-75.
Dunne et al., "Selective Expansion and Partial Activation of Human NK Cells and NK Receptor-Positive T Cells by IL-2 and IL-15," J. Immunol., 2001167(6):3129-38.
European Supplementary Search Report in European Application No. 15862930.3, dated May 30, 2018, 8 pages.
Extended European Search Report in European Appln. No. 20216695.5, dated Aug. 16, 2021, 9 pages.
Frias et al., "Generation of functional natural killer and dendritic cells in a human stromal-based serum-free culture system designed for cord blood expansion" Experimental Hematology, 2008, 36(1):61-8.
Fujisaki et al., "Expansion of Highly Cytotoxic Human Natural Killer Cells for Cancer Cell Therapy," Cancer Res., May 1, 2009,69(9):4010-7.
GenBank AccesionNo. CAA56284.1, "OX 40 ligand/ gp 34 [*Homo sapiens*]", dated Oct. 7, 2008, 2 pages.
GenBank Accession No. LN874322.1, "TPA_inf: *Homo sapiens* mRNA for tumor necrosis factor ligand 5A (TNLG5A gene)," dated Nov. 28, 2019, 2 pages.
GenBank Accession No. NM_001768.7, "Homo sapiens CD8a molecule (CD8A), transcript variant 1, mRNA" dated Feb. 27, 2020, 4 pages.
GenBank AccessionNo. NM_003326.5, "*Homo sapiens* TNF superfamily member 4 (TNFSF4), transcript variant 1, mRNA" dated Nov. 23, 2018, 4 pages.
GenBank AccessionNo. NM_003811.4, "*Homo sapiens* TNF superfamily member 9 (TNFSF9), mRNA" dated Nov. 22, 2018, 4 pages.
GenBank Accestion No. NM_021803.3, "*Homo sapiens* interleukin 21 (IL21), transcript variant 1, mRNA," dated Jun. 17, 2018, 3 pages.
Gong et al., "Ex vivo expansion of natural killer cells with high cytotoxicity by K562 cells modified to co express major histocompatibility complex class I chain-related protein A, 4-1 BB ligand, and interleukin-15," Tissue Antigens, 2010, 76(6):467-75.
Goodier et al., "Lipopolysaccharide Stimulates the Proliferation of Human CD56+CD3-NK Cells: A Regulatoiy Role of Monocytes and IL-10," J. Immunology, 2000, 165(1):13 9-47.
iwai-chem.co.jp [online] "Datasheet:CellGro/CellGenix GMP Serum-free StemCell GrowthMedium (SCGM) Xeno-free", May 16, 2011, via Internet Archive: Wayback Machine URL <://web.archive.org/web/20140124200115/iwai-chem.co.jp/products/cellgenix/20802-

(56) References Cited

OTHER PUBLICATIONS 0500.pdf>, retrieved on Jul. 23, 2021, URL<iwai-chem.co.jp/products/cellgenix/20802-0500.pdf>, 1 page.
JP Office Action in Japanese Application No. 2017-525394, dated Jul. 3, 2018, 7 pages (with English Translation).
JP Office Action in Japanese Application No. 2017-525394, dated Mar. 19, 2019, 4 pages (with English Translation).
JP Office Action in Japanese Application No. 2017-525394, dated Nov. 19, 2019, 6 pages (with English Translation).
Kelly et al., "Memory CD4+ T Cells are Required for Optimal NK Cell Effector Functions against the Opportunistic Fungal Pathogen Pneumocystis murina", J. Immunology, 2013, 190:285-95.
Keridiles et al., "T cell regulation of natural killer cells", J. Experimental Medicine, Jun. 2013, 210(6):1065-8.
Kim et al., "Ex vivo activation and expansion of natural killer cells from patients with advanced cancer with feeder cells from healthy volunteers", Cytotherapy, 2013, 15:231-41.
Koehl et al., "IL-2 activated NK cell immunotherapy of three children after haploidentical stem cell transplantation," Blood Cells Molecules & Disease, Nov.-Dec. 2004, 33(3):261-6.
Li et al., "Expansion of NK cells from PBMCs using immobilized 4-1BBL and interleukin-21", International Journal of Oncology, 2015, 47:335-342.
Lim et al., "Ex Vivo Expansion of Highly Cytotoxic Human NK Cells by Cocultivation with Irradiated Tumor Cells for Adoptive Immunotherapy," Cancer Res., Apr. 15, 2013, 73(8):2598-607.
Miller et al., "Role of monocytes in the expansion of human activated natural killer cells," Blood, Nov. 1992, 80(9):2221-9.
Min, "Identification of NK cell costimulatory receptors for large-scale expansion of NK cells for adoptive immunotherapy in cancer patients ," Thesis for the degree of Doctor of Philosophy in Biomedical Science and Engineering,2018, //library.kaist.ac.kr/search/detail/view.do?bibCtrlNo=827940&flag=dissertation.
Mingari et al., "In Vitro Proliferation and Cloning of CD3-CD16+ Cells from Human Thymocyte Precursors", J. Exp. Med., Jul. 1991, 174:21-6.
Morris et al., "A high-efficiency system of natural killer cell cloning," Journal of Immunological Methods,2005, 307(1-2):24-33.
North et al., "Tumor-Primed Human Natural Killer Cells Lyse NK-Resistant Tumor Targets: Evidence of a Two-Stage Process in Resting NK Cell Activation," J. Immunology, 2007, 178(1):85-94.
PCT International Preliminary Report on Patentability in International Appln. No. PCT/KR2015/012700, dated May 30, 2017, 6 pages.
PCT International Search Report and Written Opinion in International Appln. No. PCT/KR2015/012700, dated Feb. 29, 2016, 9 pages.
Perez et al., "A potential role for hydrocortisone in the positive regulation of IL-15-activated NK-cell proliferation and survival," Blood, Jul. 2005, 106(1):158-66.
Poggi et al., "Extrathymic differentiation of T lymphocytes and natural killer cells from human embryonic liver precursors", Proc. Natl. Acad. Sci. USA, May 1993, 90:4465-9.
sigmaaldrich.Com, "Sigma-Aldrich H9", retrieved on Nov. 15, 2019, retrieved from URL <sigmaaldrich.com/catalog/productUsigma/cb_85050301?lang=en&region=US&cm_sp=Insite-_-prodRecCold_xviews-_-prodRecCold10-1>, 3 pages.
Vansdol et al., "Generation of Functional CD56+ Natural Killer (NK) Cells from Ex Vivo Expanded Human Cord Blood (CB) Hematopoietic Stem Cells", Blood, 2000, Abstract#424, 96(11):128b.
thermofisher.com [online] "CTS (TM) AIM V (R) Medium", Aug. 24, 2015, retrieved from URL<thermofisher.com/order/catalog/product/0870112BK?ICID=search-product>, 4 pages.
Xiao-Hong et al., "Ex vivo expansion of highly purified NK cells from human peripheral blood",Zhongguo shi yan xue ye xue za zhi . . . , Apr. 2007, 15(2):373-7.
U.S. Appl. No. 14/367,813 (Corresponds to U.S. Pat. No. 9,834,753 cited in an IDS on Jan. 13, 2022), Min et al., filed Jun. 20, 2014.

U.S. Appl. No. 16/702,978, Min et al., filed Dec. 4, 2019.
U.S. Appl. No. 16/613,601 (Corresponds to US 2020/0108096 cited in an IDS on Aug. 29, 2022), Min et al., filed Nov. 14, 2019.
U.S. Appl. No. 17/293,835, Kim et al., filed May 13, 2021.
U.S. Appl. No. 17/040,661 (Corresponds to US 2021/0147803 cited in an IDS on Aug. 29, 2022), Hwang et al., filed Jan. 14, 2021.
Carswell et al., "Culture of Human T Cells in Stirred Bioreactors for Cellular Immunotherapy Applications: Shear, Proliferation, and the IL-2 Receptor," Biotechnology & Bioengineering, May 5, 2000, 68(3):328-338.
Granzin et al., "Fully automated expansion and activation of clinical-grade natural killer cells for adoptive immunotherapy," Cytotherapy, May 2015, 17(5):621-632.
Granzin et al., "Highly efficient IL-21 and feeder cell-driven ex vivo expansion of human NK cells with therapeutic activity in a xenograft mouse model of melanoma," OncoImmunology, 2016, 5(9):e1219007.
Granzin, "Highly Efficient Activation and Expansion of Natural Killer Cells For Clinical Use in Cancer Immunotherapy," Dissertation for the Degree of Doctor of Natural Sciences, Combined Faculties for the Natural Sciences and for Mathematics of the Ruperto-Carola University of Heidelberg, Germany, Apr. 25, 2016, 136 pages.
Peirson et al., "Production of Human Natural Killer Cells for Adoptive Immunotherapy Using a Computer-Controlled Stirred-Tank Bioreactor," Journal of Hematotherapy, 1996, 5(5):475-483.
Ahn et al., "Irradiated and Activated Autologous PBMCs Induce Expansion of Highly Cytotoxic Human NK Cells In Vitro," Journal of Immunotherapy, Sep. 2013, 36(7):373-381.
Claims from Chinese Application No. 201580063858.5 available on Global Dossier with a submission date of Oct. 4, 2020, with English Translation, 4 pages.
Granzin et al., "Shaping of Natural Killer Cell Antitumor Activity by Ex Vivo Cultivation," Frontiers in Immunology, Apr. 26, 2017, 8:458, 18 pages.
Hassell et al., "Adaptation to non-ammoniagenic medium and selective substrate feeding lead to enhanced yields in animal cell cultures," Journal of Cell Science, Jul. 1990, 96(3):501-508.
Kim et al., "Engineering Conferences International ECI Digital Archives Scale-up study for ex-vivo expansion of allogeneic natural killer cells in stirred-tank bioreactor," Advancing Manufacture of Cell and Gene Therapies VI, Jan. 2019, 3 pages.
Lee et al., "Expansion of cytotoxic natural killer cells using irradiated autologous peripheral blood mononuclear cells and anti-CD 16 antibody," Scientific Reports, Sep. 11, 2017, 7(1):1-13.
Min et al., "Harnessing novel engineered feeder cells expressing activating molecules for optimal expansion of NK cells with potent antitumor activity," Cellular & Molecular Immunology, Sep. 27, 2021, 19(2):296-298.
Min et al., "Optimization of Large-Scale Expansion and Cryopreservation of Human Natural Killer Cells for Anti-Tumor Therapy," Immune Network, Jan. 1, 20118, 18(4):e31, 13 pages.
Park et al., "CD4 T-cells transduced with CD80 and 4-1BBL mRNA induce long-term CD8 T-cell responses resulting in potent antitumor effects," Vaccine, Nov. 2014, 32: 6919-6926.
Parkhurst et al., "Adoptive Transfer of Autologous Natural Killer Cells Leads to High Levels of Circulating Natural Killer Cells but Does Not Mediate Tumor Regression," Clinical Cancer Research, Oct. 1, 2011, 17(19):6287-6297.
Sakamoto et al., "Phase I clinical trial of autologous NK cell therapy using novel expansion method in patients with advanced digestive cancer," Journal of Translational Medicine, Aug. 25, 2015, 13:277, 13 pages.
Yang et al., "Phase I Study of Random Healthy Donor-Derived Allogeneic Natural Killer Cell Therapy in Patients with Malignant Lymphoma or Advanced Solid Tumors," Cancer Immunology Research, Mar. 1, 2016, 4(3):215-224.

\* cited by examiner

METHOD FOR CULTURING NATURAL KILLER CELLS USING T CELLS

CLAIM OF PRIORITY

This application is a continuation application and claims priority to U.S. patent application Ser. No. 15/527,752, filed on May 18, 2017, which is a U.S. National Stage of International Application No. PCT/KR2015/012700, filed on Nov. 25, 2015, which claims priority to Korean Patent Application No. 10-2014-0166705, filed on Nov. 26, 2014, which are incorporated by reference herein.

TECHNICAL FIELD

The present invention relates to a method for producing natural killer cells using T cells, and more particularly, to a method for producing natural killer cells, which comprises culturing seed cells using CD4(+) T cells as feeder cells.

BACKGROUND ART

As therapy for preventing the metastasis and recurrence of cancer and extending the survival time of terminal cancer patients, immunotherapy based on the immune function of patients is receiving attention. In recent years, immunotherapy with genetically engineered T cells expressing antigen-specific chimeric antigen receptors (CARs) has been recognized as a promising approach for cancer therapy. However, when T cells of other people are used, they can cause series graft-versus-host disease (GVHD) due to major histocompatibility complex (MHC) restriction. For this reason, for commercialization of cell therapy, natural killer (NK) cells are much more useful, which can be used for allogeneic transplantation and are possible to produce in large amount and to freeze.

Natural killer cells are known as lymphoid cells that account for about 10-15% of peripheral blood lymphocytes and play an important role in innate immune responses. Unlike T cells, natural killer cells recognize their target in an MHC non-restricted manner, and activating receptors (such as NKG2D, NCR (NKp30, NKp44, or NKp46)) in natural killer cells compete with inhibitory receptors such as KIR or CD94/NKG2A to display activity and eliminate tumor target cells. Natural killer cells can exhibit antiviral effects, anti-GvH effects, and anticancer effects. Particularly, natural killer cells directly kill malignant tumors, including sarcoma, myeloma, carcinoma, lymphomas and leukemia, or contribute to adaptive immune activation by inducing dendritic cell (DC) activity or tumor-specific cytotoxic T lymphocytes (CTLs), thereby eliminating abnormal cells which are tumor cells or cells developing into tumor cells.

The anticancer effects of natural killer cells were demonstrated through allogeneic hematopoietic stem cell transplantation, and it was found that donor natural killer cells inhibit microtumor remaining after transplantation of T cell-depleted hematopoietic stem cells. In addition, because the graft-versus-tumor (GVT) effect of donor natural killer cells significantly increases when there is KIR (killer cell immunoglobulin-like receptors)—MHC mismatch between the donor and the recipient, the allogeneic natural killer cells is much more effective than the use of the cancer patient's own autologous natural killer cells having reduced function. Despite the potential of such natural killer cells as therapeutic agents against cancers or infectious diseases, most natural killer cells in the body of normal people exist in a resting state, and natural killer cells in the body of cancer patients lack their function due to the immune escape mechanism of cancer cells. In order to actually use natural killer cells as therapeutic agents, activated natural killer cells capable of recognizing and destroying tumor cells are required, and for this reason, it is very important to activate natural killer cells by ex vivo expansion culture from normal culture or patient's blood. In addition, because the number of natural killer cells in vivo is limited, it is necessarily required to develop a technology capable of producing and freezing natural killer cells in large amounts that can sufficiently exhibit anticancer effects.

In ex vivo expansion culture of natural killer cells, PBMC, CD3− cells, CD3-CD56+ cells, CD56+ cells or the like are used as seed cells, and cytokines such as IL-2, IL-12, IL-15 or IL-21, and OKT-3 antibody (Condiotti et al., *Experimental Hematol.* 29(1):104-113, 2001) stimulating LPS (Goodier et al., *J. Immunol.* 165(1):139-147, 2000) and CD3, are used as growth factors for natural killer cells. However, the use of the above-mentioned growth factors alone allows natural killer cells to increase about 3-10-fold and cannot achieve sufficient proliferation. For this reason, in several studies, there was an attempt to proliferate natural killer cells using various types of feeder cells. It has been reported that the use of the leukemia cell line CTV-1 showed little or no improvement in proliferation (North et al., *J. Immunol.* 178(1):85-94, 2007), and culture with EBV-LCL for 21 days resulted in an increase in cell number of an average of about 490-fold (Berg et al., *Cytotherapy,* 11(3): 341-355, 2009). It has been reported that, when culture was performed for 7 days to 3 weeks using artificial APCs (antigen presenting cells) obtained by expressing 4-1 BBL and membrane-bound IL-15 in the K562 cell line, cell number increased an average of 90-209-fold (Fujisaki et al., *Cancer Res.* 69(9):4010-4017, 2009). In addition, it has been reported that when a K562 cell line having the MICA, 4-1BBL and IL-15 expressed therein was cultured for 3 weeks, cell number increased an average of 350-fold (Gong et al., *Tissue Antigens,* 76(6):467-475, 2010), and when a K562 cell line having membrane-bound IL-15 expressed therein was cultured for 3 weeks while the cells were re-stimulated at 7-day intervals, cell number increased an average of 21,000-fold (Denman et al., *PlosOne,* 7(1): e30264, 2012). In addition, it has been reported that, when PBMCs were cultured for 14 days using KL-1 (human T lymphoblast) and EBV-transformed B cells as feeder cells, an average of a 740-fold increase in the number of natural killer cells was induced (Lim et al., *Cancer Res.,* 73(8): 2598-6607, 2013).

In Korean Patent No. 10-1133185, the present inventors have disclosed that PBMCs stimulated with OKT-3 can be used as feeder cells, and also disclosed that, when the PBMCs were cultured for 14 days, a 691-fold increase in cell number could be induced (Lim et al., *PlosOne,* 7(1): e53611, 2012). In addition, the present inventors have disclosed that, when PBMCs were re-stimulated twice or more with feeder cells, an increase of thousands to tens of thousands of times in cell number could be induced (WO2013/094988). However, in the case of mass culture, the required amounts of PBMCs for use as feeder cells increases and the results of culture of natural killer cells change depending on the characteristics of each donor, and for these reasons, it is actually difficult to achieve the smooth supply and mass culture of raw materials for commercialization and the management of donors.

Accordingly, the present inventors have made extensive efforts to develop seed cells capable of substituting for PBMCs, and as a result, have found that among PBMCs, T lymphocytes, particularly helper T cells (Th cells), are very important in the proliferation of natural killer cells, and T-cell leukemia-lymphoma cell lines which can proliferate while having the characteristics of Th cells can selectively induce the culture of natural killer cells and allow natural killer cells to stably proliferate, thereby completing the present invention.

DISCLOSURE OF INVENTION

Technical Problem

It is an object of the present invention to provide a method of producing natural killer cells by culturing and proliferating the cells in an efficient and stable manner.

Another object of the present invention is to provide natural killer cells produced by the above method, a composition for preventing or treating cancer or infectious disease, which comprises the natural killer cells as an active ingredient, and a method for preventing or treating cancer or infectious disease, comprising administering to a subject in need thereof a therapeutically effective amount of the above composition.

Technical Solutions

To achieve the above objects, the present invention provides a method for producing natural killer cells, wherein T cells, particularly CD4(+) T cells, are used as feeder cells that stimulate the natural killer cells.

The present invention also provides natural killer cells produced by the above method.

The present invention also provides a composition for preventing or treating cancer or infectious disease, which comprises the above natural killer cells as an active ingredient.

The present invention also provides a method for preventing or treating cancer or infectious disease, administering to a subject in need thereof a therapeutically effective amount of the above composition.

BEST MODE FOR CARRYING OUT THE INVENTION

Figure 1A:
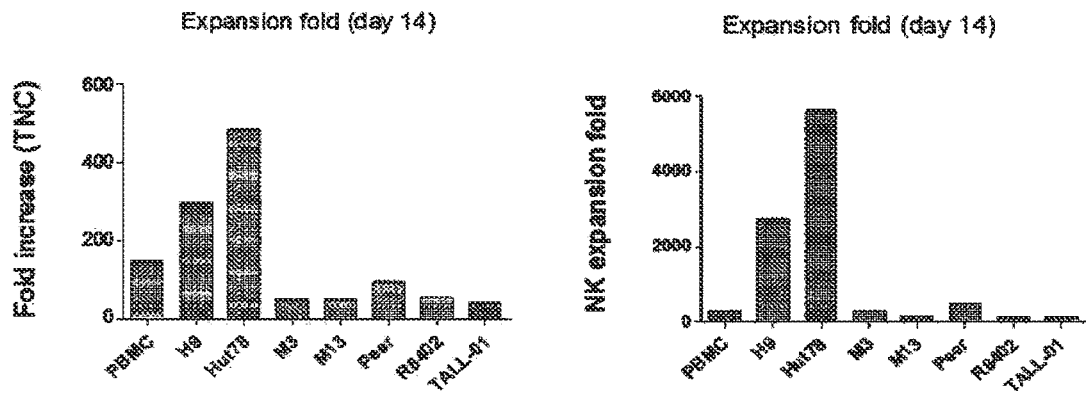
FIG. 1a shows the results of measuring the increase in the number of total nucleated cells and natural killer cells, obtained by culturing PBMC seed cells using various T cells as feeder cells for 14 days (condition 1 in Table 1 below).

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In the present invention, it was found that, in a process of producing natural killer cells by proliferating the cells using various T cells as feeder cells, T cells, particularly CD4(+) T cells, induce the selective proliferation of natural killer cells, and thus the proliferation of the natural killer cells increases and the cell killing activity thereof also increases.

In one aspect, the present invention is directed to a method for producing natural killer cells, wherein CD4(+) T cells are used as feeder cells that stimulate the natural killer cells.

Concretely, the present invention is directed to a method for producing natural killer cells, wherein CD4(+) T cells isolated ex vivo, CD4(+) T cells cultured ex vivo, or CD4(+) T cell lines are used as feeder cells, and one or more types of cells selected from the group consisting of peripheral blood cells, peripheral blood leukocyte cells, peripheral blood mononuclear cells (PBMCs), enriched natural killer cells and isolated natural killer cells are used as seed cells.

The method for producing natural killer cells according to the present invention may concretely comprise the following steps, but is not limited thereto:

(i) a step of isolating peripheral blood leukocyte cells, peripheral blood mononuclear cells (PBMCs), T cell-depleted mononuclear cells or natural killer cells from human peripheral blood;

(ii) a step of culturing natural killer cells in a medium containing an interleukin protein and a T cell-stimulating antibody having a low affinity for T cells, in the presence of inactivated or non-inactivated T cells;

(iii) a step of re-stimulating the natural killer cells with T cells in a medium containing an interleukin protein and a T cell-stimulating antibody having a low affinity for T cells, and further culturing the natural killer cells.

Hereinafter, the present invention will be described in further detail.

Natural killer (NK) cells are present in an amount of about 10-15% in the blood of normal people, and have high killing ability when they react with non-self material. Natural killer cells non-specifically and immediately act in response to the infection of cells with various viruses, the penetration of bacteria or the production of abnormal cells to thereby remove foreign matter. However, the number of natural killer cells present in the body is not so large, and the number of effective natural killer cells required to exhibit therapeutic effects should be very large. For this reason, a method for the proliferation and production of effective natural killer cells is required.

Methods for proliferating natural killer cells include a method comprising isolating natural killer cells only, suitably stimulating the isolated natural killer cells with feeder cells, and proliferating the stimulated natural killer cells, and a method comprising selectively proliferating natural killer cells from peripheral blood lymphocytes (PBLs) or peripheral blood mononuclear cells (PBMCs) to thereby obtain a relatively large amount of natural killer cells. To isolate natural killer cells from peripheral blood, a conventional method known to one skilled in the art may be used, and commercially available natural killer cells may also be purchased and used.

PBMCs are separated into lymphocytes and monocytes, and the lymphocytes are further divided into T cells, B cells, and natural killer cells. Among them, the T cells are further divided into helper T cells (Th cells) and cytotoxic T cells (Tc cells). In the method of culturing natural killer cells using PBMC feeder cells, the mass proliferation of T cells is induced, and the proliferation of natural killer cells is limited, and for this reason, an expensive complex step of removing T cells is required before or after culture. Accordingly, in the present invention, whether any cell group among the PBMC groups contributes to the proliferation of natural killer cells was examined. As a result, it was found that T cells contribute to the proliferation of natural killer cells, and among them, Th cells are very important in the proliferation of natural killer cells. Based on this finding, T cells that can proliferate while having the characteristics of Th cells were used as feeder cells capable of PBMCs in the culture of natural killer cells.

As used herein, the term "feeder cells" refers to cells that produce various metabolites due to their metabolic activity to thereby assist in the proliferation of target cells, even though these cells cannot proliferate.

Feeder cells that are used in the present invention may be CD4(+) T cells isolated ex vivo, CD4(+) T cells expansion-cultured ex vivo, or a CD4(+) T cell line (T lymphoma cell line). The CD4(+) T cell line (T lymphoma cell line) that is used in the present invention is concretely H9, HuT78, Loucy, Molt3, Molt-13, PEER, RPMI8402, or TALL-01, more concretely H9 or HuT78, but is not limited thereto.

T cells that are used as the feeder cells may be inactivated or non-inactivated cells whose proliferation was inhibited. Concretely, the T cells may be inactivated to ensure their safety. As a method for inactivating the T cells, a conventional method known in the art may be used, and for example, a method of irradiating the T cells with gamma-rays may be used. If non-inactivated T cells are used, they can be killed by natural killer cells during culture, because they are mostly tumor cells.

The proliferation method as described in the present invention uses T cells as feeder cells. This method has an advantage in that, because the culture of natural killer cells is selectively induced in seed cells such as PBMCs without removing T cells, the culture can be stably performed without a significant difference in culture results between donors. Thus, it is possible to obtain an increased amount of natural killer cells for therapeutic purposes in an efficient and stable manner.

As used herein, the term "seed cells" means cells capable of proliferating to natural killer cells by suitable culture. Concretely, the seed cells that are used in the present invention may be one or more types selected from the group consisting of peripheral blood cells, peripheral blood leukocytes, PBMCs (peripheral blood mononuclear cells), enriched natural killer cells, and isolated natural killer cells, but are not limited thereto. More concretely, the seed cells may be CD3(+) cell-depleted cells(CD3(−) cells).

In addition, in the method for producing natural killer cells according to the present invention, natural killer cells are concretely cultured in a medium containing an interleukin protein and a T cell-stimulating antibody having a low affinity for T cells, but the scope of the present invention is not limited thereto. Herein, the T cell-stimulating antibody having a low affinity for T cells is a protein that reacts specifically with CD3 antigen, a group of molecules which associate with a T cell receptor (TCR) to form an antigen recognition complex, in which the CD3 molecule has a longer intracellular domain compared to TCR and functions to transfer an antigen recognition signal into cells. The T cell-stimulating antibody having a low affinity for T cells, which can be used in the present invention, is concretely anti-CD3 antibody, more concretely OKT-3, UCHT1, HIT3a or the like, most concretely OKT-3 antibody.

As used herein, the term "interleukin (IL) protein" refers to a collection of biologically active proteins produced by immune cells such as lymphocytes, monocytes or macrophages, and means a group of molecular species in cytokines. Examples of an interleukin protein, which may be used in the present invention, include IL-2, IL-15, IL-12, IL-18, IL-21 and the like. Concretely, the interleukin protein is IL-2 protein.

The method for producing natural killer cells according to the present invention concretely comprises: adding natural killer cells and a T lymphoma cell line to a conventional animal cell culture medium such as AIM-V medium, RIMI 1640, CELLGRO® SCGM, X-VIVO™20, IMDM or DMEM; adding an interleukin protein and T cell-stimulating antibody having a low affinity for T cells to the culture medium; and culturing the cells, but is not limited thereto. In an example of the present invention, cells were cultured in a medium containing OKT-3 antibody and IL-2. In the present invention, OKT-3 antibody is used at a concentration of 0.1-100 ng/ml, concretely about 10 ng/ml, and IL-2 is used at a concentration of 10-2000 U/ml, concretely about 500 U/ml. In addition, the culture medium may further contain serum or plasma and an additional growth factor that supports the proliferation of lymphocytes. The type of serum or plasma that is added to the medium is not specifically limited, and thus various types of commercially available serum or plasma may be used in the present invention. Concretely, autologous human serum or plasma is used in the present invention.

The method for producing natural killer cells according to the present invention comprises a step of culturing natural killer cells in a medium containing an interleukin protein and a T cell-stimulating antibody having a low affinity for T cells, in the presence of T cells as feeder cells that stimulate natural killer cells. For use in the culturing step, the feeder cells and the seed cells are concretely mixed at a ratio of at least 1:1, more concretely 2:1-20:1, most concretely 5:1, but are not limited thereto. Herein, the term "ratio" refers to a ratio based on cell number.

In addition, in the method for producing natural killer cells according to the present invention, the stimulation and culture of natural killer cells with CD4(+) T cells serving as feeder cells may be repeatedly performed in order to obtain an increased number of natural killer cells. Thus, the method of the present invention may further comprise re-stimulating natural killer cells at a feeder cell-to-seed cell ratio of at least 1:1, concretely 2:1-20:1, most concretely 5:1. Herein, the term "ratio" refers to a ratio based on cell number.

The CD4(+) T cells that are used in the re-stimulation are concretely H9 or HuT78 cells, but are not limited thereto. In addition, inactivated cells whose proliferation was inhibited, or non-inactivated cells, may be used in the re-stimulation.

In addition, the re-stimulation is concretely performed in a medium containing an interleukin protein and a T cell-stimulating antibody having a low affinity for T cells, at intervals of 5-12 days, more concretely 7 days, but is not limited, and may be repeated at least once. The method of the present invention may further comprise, after the step of culturing the cells in the medium containing the interleukin protein and the T cell-stimulating antibody having a low affinity for T cells, a step of culturing the cells in a medium free of the antibody.

Herein, the T cell-stimulating antibody having a low affinity for T cells may be an anti-CD3 antibody, concretely at least one selected from the group consisting of OKT3, UCHT1 and HIT3a antibodies, most concretely OKT3 antibody, and the interleukin protein may be at least one selected from the group consisting of IL-2, IL-12, IL-15, IL-18, and IL-21, concretely IL-2.

As used herein, the term "stimulating" means inducing the proliferation of natural killer cells by adding feeder cells or the like. In the stimulation step, a T cell-stimulating antibody having a low affinity for T cells may also be used. As used herein, the term "re-stimulating" means re-inducing the proliferation of natural killer cells by adding feeder cells and/or a T cell-stimulating antibody, which has a low affinity for T cells, to the medium after a certain time of culture.

In the method of the present invention, the natural killer cells are cultured for at least 5 days, concretely 5-60 days, more concretely 14-21 days, but are not limited thereto.

The stimulation may start at day 0 of culture and may be repeated at intervals of 5-12 days, concretely 7 days, but is not limited thereto. The cells may be harvested at 5 days or more, concretely 14 days, after the final stimulation, but are not limited thereto.

Natural killer cells cultured according to the method of the present invention as described above can be frozen and are not functionally impaired even when they are thawed. In addition, these cells express higher levels of activating receptors such as NKp44 and NKp46 compared to conventional cells cultured using PBMCs as feeder cells, and thus have increased abilities to kill tumor cells and to secrete cytokines, indicating that these cells can exhibit excellent anticancer effects. Thus, according to the present invention, a cell therapeutic agent effective for tumor treatment can be prepared using a large amount of activated natural killer cells that can be clinically applied.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Preparation of PBMCs and Various T Cells 1-1: Preparation of PBMC Seed Cells and CD3(+)—Depleted Seed Cells Peripheral blood mononuclear cells (PBMCs) were dispensed into vials and frozen in liquid nitrogen. One frozen PBMC vial was thawed and transferred into a 50 mL tube, and the cells were suspended in 20 mL of PBS (phosphate buffered saline) containing 1 vol % FBS (fetal serum bovine) or autoplasma and were centrifuged at 1200 rpm at 4° C. for 10 minutes. The PBMC pellets were suspended in 10 mL of MACS running buffer, and the cells were counted using an Adam cell counter system.

$1 \times 10^7$ PBMC seed cells were dispensed into each of 50 mL tubes. To obtain PBMC feeder cells and CD3(+) cell-depleted seed cells, $5 \times 10^7$ cells were transferred into each of 50 mL fresh tubes and centrifuged at 1200 rpm at 4° C. for 10 minutes. In the case of PBMC feeder cells, the cell pellets were suspended in 10 mL of 1 vol % autoplasma-containing CELLGRO® medium (Cellgenix).

To obtain CD3(+)—depleted seed cells, 400 μL of MACS running buffer and 100 μL of CD3 magnetic beads (Miltenyi biotech) were added to $5 \times 10^7$ PBMC cell pellets which were then incubated at 4° C. for 20 minutes. The resulting cells were washed with 10-20 mL of MACS running buffer, and then centrifuged at 1200 rpm at 4° C. for 10 minutes and suspended aging in 2 mL of MACS running buffer. The cells were separated using a CS column (Miltenyi Biotech, 130-041-305) equipped with VarioMACS (Miltenyi Biotech), and the column was washed to reach a final volume of 20 mL, thereby recovering the cells. The cells were counted using an Adam cell counter system, and $1 \times 10^7$ cells were dispensed into 50 mL fresh tubes and centrifuged at 1200 rpm at 4 L for 10 minutes. The cell pellets were suspended in 10 mL of CELLGRO® medium (Cellgenix) containing 1 vol % autoplasma.

1-2: PBMC Feeder Cells and Various T Feeder Cells $5 \times 10^7$ PBMC feeder cell pellets separated in Example 1-1 were suspended in 10 mL of 1 vol % autoplasma-containing CELLGRO® medium (Cellgenix) and irradiated with 2000 cGy of gamma rays in a gamma-ray irradiator, thereby preparing PBMC feeder cells.

Various T cells were recovered from culture flasks and centrifuged at 1200 rpm at 4 L for 10 minutes, and then $5 \times 10^7$ cells were dispensed into each tube and centrifuged at 1200 rpm at 4° C. for 10 minutes. The T cells were suspended in 5 mL of 1 vol % autoplasma-containing CELLGRO® medium (Cellgenix), and then irradiated with 15000-30000 cGy of gamma rays in a gamma ray irradiator, thereby preparing T cells for use as feeder cells.

Example 2: Culture of Natural Killer Cells Using Various T Cells as Feeder Cells Conditions for culturing PBMC seed cells and CD3(+)-depleted seed cells using T cells as feeder cells are shown in Table 1 below.

In the case of conditions 1 and 3 shown in Table 1, the cells were counted at days 3-5 of culture, and diluted to a density of about $2-5 \times 10^5$ cells/mL with CELLGRO® medium (Cellgenix) containing 500 IU of IL-2 (Proleukin) and 1 vol % autoplasma. The diluted cells were stationary-cultured again in a suitable culture vessel. Next, the cells were suspension-cultured up to day 14 while the cells were counted at intervals of 2-3 days and diluted to a density of $5-10 \times 10^5$ cells/mL CELLGRO® medium (Cellgenix) containing 500 IU of IL-2 and 1 vol % autoplasma. At day 14 of suspension culture, natural killer cells were harvested.

The proliferation rates of the natural killer cells cultured under condition 1 were compared, and as a result, it was shown that PBMC feeder cells showed a 147-fold increase in the number of total nucleated cells (TNCs), and H9 feeder cells and HuT78 feeder cells showed a 298-fold increase and a 485-fold increase, respectively, which were significantly higher than the fold increase shown by PBMC feeder cells. Also, in the proliferation rate of natural killer cells among total nucleated cells, PBMC feeder cells showed a 247-fold increase in the number of natural killer cells, H9 feeder cells showed a 2752-fold increase which was about 10 times higher than that shown by PBMC feeder cells, and HuT78 feeder cells showed a 5649-fold increase which was about 20 times higher than that shown by PBMC feeder cells. In addition, other T cells showed proliferation rates lower than that shown by PBMCs (see FIG. 1a).

Figure 1B:
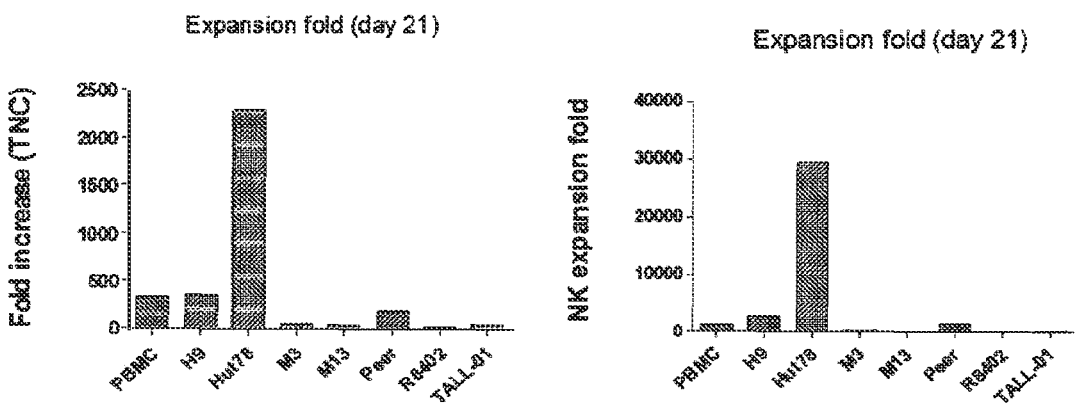
FIG. 1b shows the results of measuring the increase in the number of total nucleated cells and natural killer cells, obtained by culturing PBMC seed cells using various T cells as feeder cells, and then re-stimulating the cells with various T cells serving as feeder cells, and culturing the cells up to day 21 (condition 2 in Table 1 below).
Figure 1C:
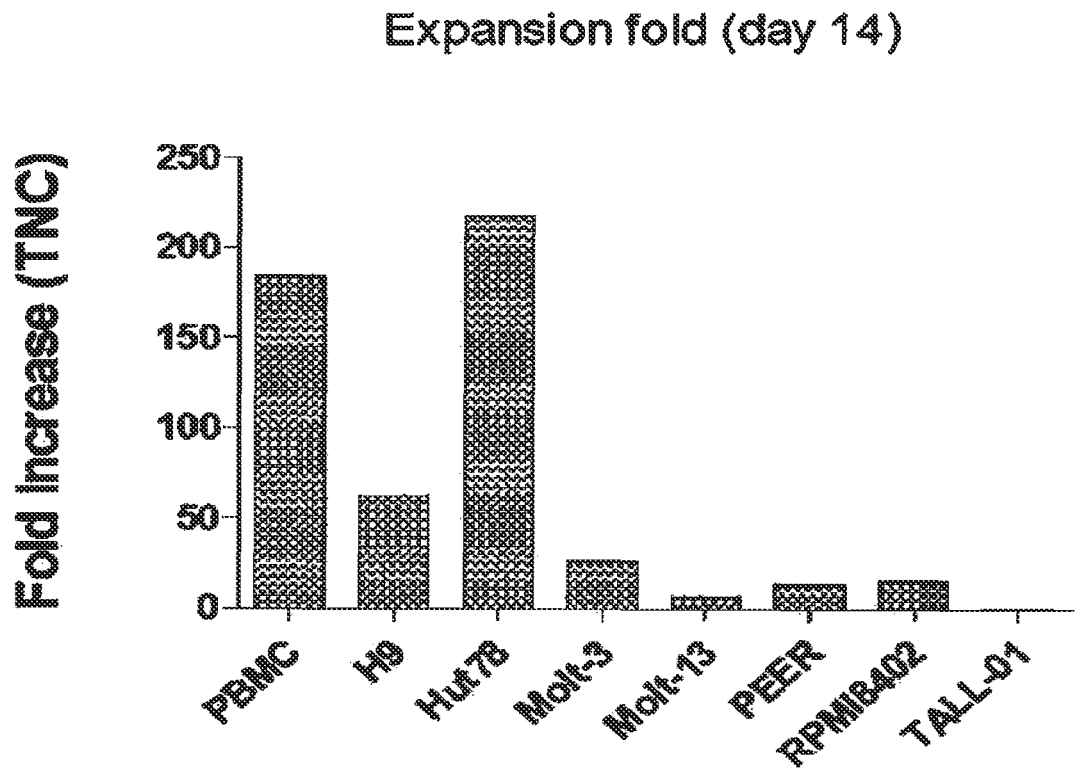
FIG. 1c shows the results of measuring the increase in the number of total nucleated cells and natural killer cells, obtained by culturing CD3(+) cell-depleted PBMC seed cells using various T cells as feeder cells for 14 days (condition 3 in Table 1 below).

In addition, the proliferation rates of natural killer cells cultured under condition 3 were compared, and as a result, PBMCs showed a 184-fold increase in the number of total nucleated cells, H9 feeder cells showed a 62-fold increase, and HuT78 feeder cells showed a 217-fold increase (see FIG. 1c). Other T cells all showed proliferation rates lower than that shown by H9.

2-2: Re-Stimulation Conditions in 21-Day Culture

For culture of natural killer cells, 500 IU of IL-2 and 10 ng/mL of OKT-3 were added to a culture vessel (a flask or a cell culture bag). At day 0 of culture, PBMC seed cells and PBMC feeder cells or T feeder cells were added to the

TABLE 1

|  | Seed cells | Feeder cells | | Culture period |
| --- | --- | --- | --- | --- |
|  |  | D0 stimulation | D7 stimulation |  |
| Condition 1 | PBMC | PBMC & T lymphoma | None | 14 days |
| Condition 2 | PBMC | PBMC & T lymphoma | PBMC & T lymphoma | 21 days |
| Condition 3 | CD3(−) | PBMC & T lymphoma | None | 14 days |
| Condition 4 | CD3(−) | PBMC | PBMC & T lymphoma | 21 days |

2-1: 14-Day Culture Conditions

For culture of natural killer cells, 500 IU of IL-2 and 10 ng/mL of OKT-3 were added to a culture vessel (a flask or a cell culture bag). At day 0 of culture, PBMC seed cells and PBMC feeder cells or T feeder cells were added to the culture vessel at a ratio of 1:5 in an amount of 0.5-10 mL for each cell type, and 0.5-10 mL of 1 vol % autoplasma containing CellGro medium (Cellgenix) was added to the cells which were then stationary-cultured in an incubator at 37° C. for 3-5 days (condition 1). In addition, at day 0 of culture, CD3(−) seed cells and PBMC feeder cells or T seed cells were added to a culture vessel at a ratio of 1:5 in an amount of 0.5-10 mL for each cell type, and 0.5-10 mL of 1 vol % autoplasma-containing CELLGRO® medium (Cellgenix) was added to the cells which were then stationary-cultured in an incubator at 3° C. for 3-5 days (condition 3).

culture vessel at a ratio of 1:5 in an amount of 0.5-10 mL for each cell type, and 0.5-10 mL of 1 vol % autoplasma-containing CELLGRO® medium (Cellgenix) was added to the cells which were then stationary-cultured in an incubator at 37° C. for 3-5 days (condition 1). For re-stimulation at day 7 of culture, natural killer cells, stimulated and cultured with PBMC feeder cells at day 0, were re-stimulated with PBMC feeder cells and various T feeder cells, and cells, stimulated and cultured with T feeder cells at day 0, were re-stimulated using the same cells as feeder cells (condition 2). In addition, at day 0 of culture, CD3 (−) seed cells and PBMC feeder cells were added to a culture vessel at a ratio of 1:5 in an amount of 0.5-10 mL for each cell type, and 0.5-10 mL of 1 vol % autoplasma-containing CELLGRO® medium was added to the cells which were then stationary-cultured in an incubator at 37° C. for 3-5 days, thereby achieving the first stimulation of natural killer cells. In this case, for restimulation at day 7 of culture, natural killer cells were re-stimulated with PBMC feeder cells and various T feeder cells and cultured for 21 days (condition 4).

For re-stimulation at day 7 of culture, the natural killer cells being cultured were counted and diluted to a density of 2-5×10$^5$ cells/mL with 1 vol % autoplasma-containing CELLGRO® medium (Cellgenix), and PBMC and T feeder cells were diluted 3- to 10-fold and suspended in 1 vol % autoplasma-containing CELLGRO® medium (Cellgenix), and then inactivated by irradiation with 2000 and 15000-30000 cGy of gamma-rays, respectively, in a gamma-ray irradiator. 500 IU of IL-2 and 10 ng/mL of OKT-3 were added to the medium, and the prepared two types of cells were co-cultured. Next, the cells were suspension-cultured up to day 21 while the cells were counted at intervals of 2-3 days and diluted to a density of 5-10×10$^5$ cells/mL with CELLGRO® medium (Cellgenix) containing 500 IU of IL-2 and 1 vol % autoplasma. At day 21 of suspension culture, natural killer cells were harvested.

The proliferation rates of natural killer cells cultured under condition 2 in Table 1 were compared. As a result, it was shown that the fold increase in the number of total nucleated cells was higher in the order of PBMCs (334-fold), H9 (358-fold) and HuT78 (2282-fold). The fold increase in the number of natural killer cells was 1257-fold for PBMCs, 2677-fold for H9, and 29455-fold for HuT78 (FIG. 1b).

Figure 1D:
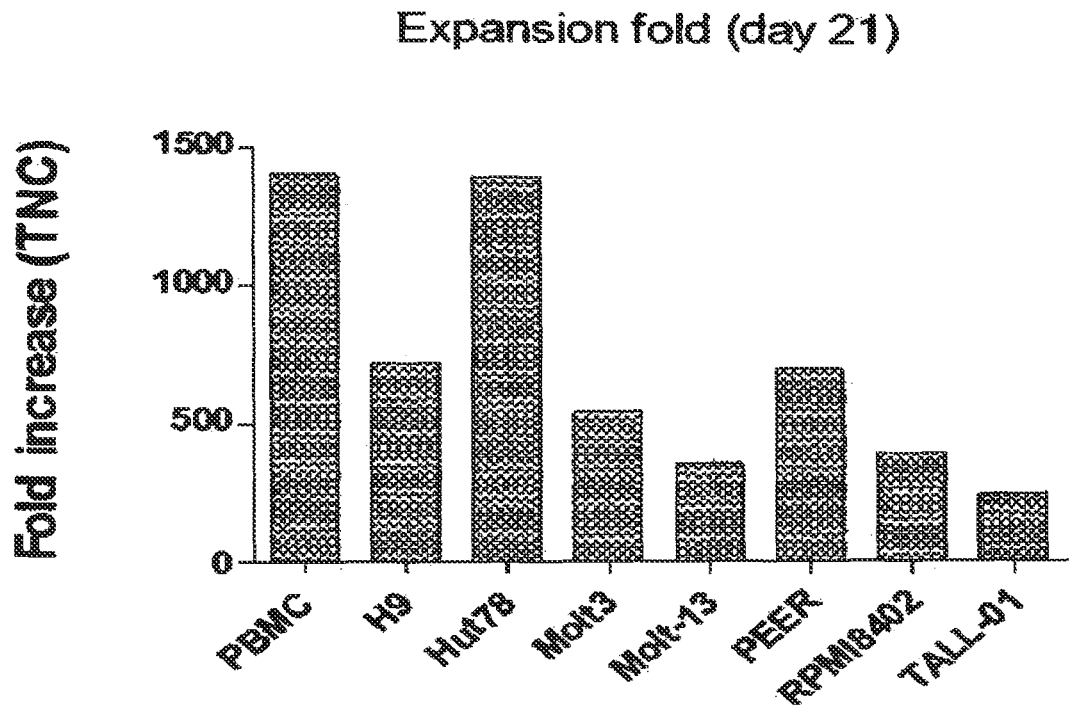
FIG. 1d shows the results of measuring the increase in the number of total nucleated cells and natural killer cells, obtained by culturing CD3(+) cell-depleted PBMC seed cells using PBMC feeder cells, and then re-stimulating the cells with various T cells serving as feeder cells, and culturing the cells up to day 21 (condition 4 in Table 1 below).

In addition, the proliferation rates of natural killer cells cultured under condition 4 of Table 1 while performing first stimulation with PBMC feeder cells and second stimulation with PBMC feeder cells and each type of T feeder cells were compared. As a result, it was shown that the fold increase in the number of total nucleated cells was 1402-fold for PBMCs, 720-fold for H9, and 1393-fold for HuT78 (FIG. 1d). Other T cells showed an increase in cell number of about 500-fold.

As described above, it could be seen that, in 14-day culture and 21-day culture, H9 and HuT78 can be used as feeder cells that are very excellent in terms of proliferation rate compared to PBMCs.

The results of evaluation performed using CD3(-) cells as seed cells and various T cells as feeder cells did slightly differ from the results obtained using PBMCs as feeder cells. Specifically, the proliferation rate of natural killer cells was similar between the PBMC feeder cells and the HuT78 feeder cells, and H9 feeder cells showed a reduced proliferation rate of natural killer cells compared to the PBMC feeder cells.

2-3: Culture of Poorly Proliferating Donor Cells

Donor cells that showed poor proliferation when cultured with PBMC feeder cells under condition 4 of Table 1 were selected and used to compare the proliferation rates of natural killer cells.

Figure 1E:
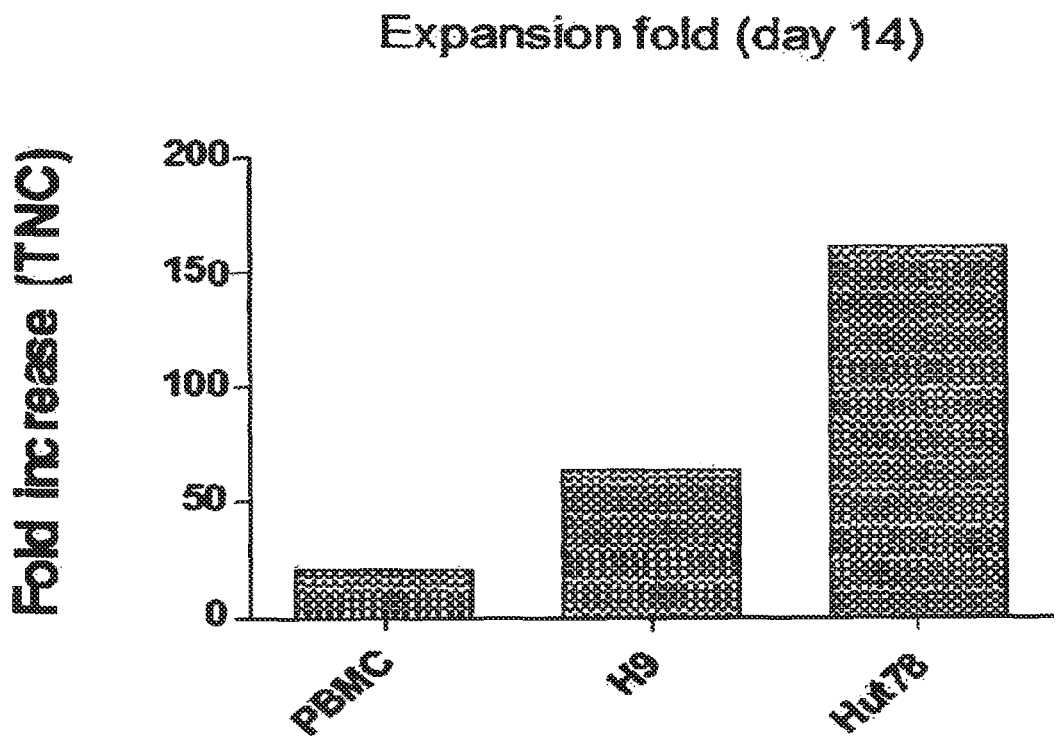
FIG. 1e shows the results of measuring the increase in the number of total nucleated cells of poorly proliferating donors, cultured under condition 3 of Table 1 below.

As a result, it was shown that culture with PBMC feeder cells showed an average of a 21-fold increase in the number of natural killer cells, but H9 and HuT78 showed a 64-fold increase and a 161-fold increase, respectively. Particularly, HuT78 showed an increase in cell number, which was about 8 times higher than that shown by PBMC feeder cells (FIG. 1e). Thus, it could be seen that T feeder cells can overcome the difference between donors with respect to the proliferation of natural killer cells, unlike PBMC feeder cells.

In the case of PBMC feeder cells, a process of depleting T cells from seed cells is necessarily required, because the proliferation of T cells rather than natural killer cells is induced when T cells are present in seed cells. In addition, a preculture process for previously selecting donors is required, because the difference in proliferation rate between donors is significant. However, it was found that T cells, particularly CD4-expressing T cells, could induce the selective proliferation of natural killer cells regardless of the presence or absence of T cells in seed cells and that the proliferation of poorly proliferating donor cells could also be easily induced when culture with PBMC feeder cells was performed.

Example 3: In Vitro Cell Viability

Among cell counter systems employing a PI dye capable of binding to the intracellular nucleus, an ADAM cell counter system was used to comparatively evaluate in vitro cell viabilities. The number of viable cells was determined by subtracting the measured dead cell count from the measured total cell count, and then cell viability was calculated using the following equation.

Cell viability (%)=(viable cell count/total cell count)×100

Figure 2:
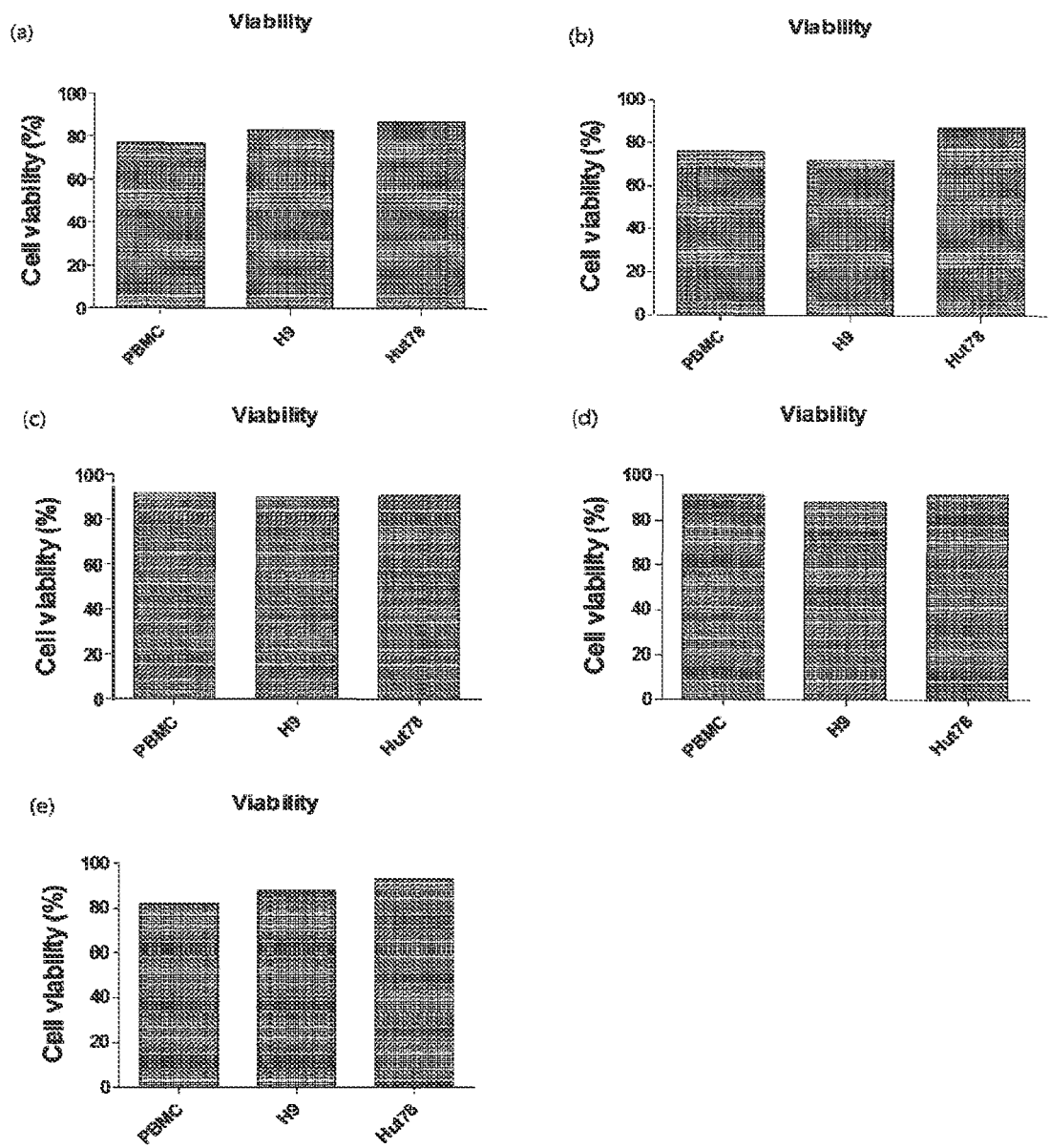
FIG. 2 shows the cell viabilities of natural killer cells cultured using various T cells as feeder cells. (a): cell viability of natural killer cells cultured under condition 1 shown in Table 1; (b) : cell viability of natural killer cells cultured under condition 2 shown in Table 1; (c): cell viability of natural killer cells cultured under condition 3 shown in Table 1; (d): cell viability of natural killer cells cultured under condition 4 shown in Table 1; and (e) cell viability of natural killer cells of poorly proliferating donors, cultured under condition 2 shown in Table 1.

The viability of natural killer cells was measured after culture under conditions 1 and 2 (that is, 14-day culture and 21-day culture of PBMC seed cells with various feeder cells) shown in Table 1. As a result, it was shown that the use of PBMC feeder cells showed a viability lower than 80%, and H9 and HuT78 showed a viability of 80% or higher (FIGS. 2a and 2b).

The viability of natural killer cells was measured after culture under conditions 3 and 4 (that is, 14-day culture and 21-day culture of CD3(+) T cell-depleted seed cells with various T feeder cells) shown in Table 1 were measured. As a result, it was shown that a high viability of about 90% or higher was shown in all the conditions. In the case of poorly proliferating donor cells, PBMC feeder cells showed a viability of 82%, and HuT78 showed a viability of 93% which was at least 10% higher than that shown by PBMC feeder cells (FIGS. 2c and 2d).

The viability of the cells cultured using PBMCs and various T feeder cells for 14 days or 21 days was generally higher in CD3(-) seed cells than in PBMC seed cells, and showed no significant difference between the types of seed cells. However, in the case of poorly proliferating donor cells, HuT78 showed a viability which was about 10% higher than that shown by PBMC feeder cells.

Thus, it could be seen that HuT78 cells are feeder cells for culturing natural killer cells, which are useful in terms of cell viability compared to PBMCs.

Example 4: In Vitro Analysis of Cell Phenotypes

Natural killer cells cultured according to the methods of Examples 1 and 2 were collected before and after culture and centrifuged at 1200 rpm for 5 minutes, and the medium was removed by suction. The cells were diluted with 1 mL of FACS buffer (2.5% FBS-containing PBS), counted, and then diluted to a density of 5×10$^6$ cells/mL with FACS buffer. 100 L of the diluted cell solution was dispensed into each of 5 mL FACS tubes (Falcon, 352052), and the phenotypes of the cells were analyzed using the following antibody:

Tube 1: anti-human CD3-FITC (BD Pharmingen, 555332), anti-human CD16-PE (BD Pharmingen, 555407), anti-human CD56-PE-Cy5 (BD Pharmingen, 555517)

Tube 2: anti-human CD14-FITC (BD Pharmingen, 555397), anti-human CD19-PE (BD Pharmingen, 555413), anti-human CD3-PE-Cy5 (BD Pharmingen, 555341)

Tube 3: anti-human CD3-FITC, anti-human NKG2A-PE (R&D system, FAB1059P), anti-human CD56-PE-Cy5

Tube 4: anti-human CD3-FITC, anti-human NKG2C-PE (R&D system, FAB138P), anti-humanCD56-PE-Cy5
Tube 5: anti-human CD3-FITC, anti-human NKG2D-PE (R&D system, FAB139P), anti-human CD56-PE-Cy5
Tube 6: anti-human CD3-FITC, anti-human NKp30-PE (BD Pharmingen, 558407), anti-human CD56-PE-Cy5
Tube 7: anti-human CD3-FITC, anti-human NKp44-PE (BD Pharmingen, 558563), anti-humanCD56-PE-Cy5
Tube 8: anti-human CD3-FITC, anti-human NKp46-PE (BD Pharmingen, 557991), anti-human CD56-PE-Cy5
Tube 9: anti-human CD3-FITC, anti-human DNAM-1-PE (BD Pharmingen, 559789), anti-humanCD56-PE-Cy5
Tube 10: anti-human CD3-FITC, anti-human CD25-PE (BD Pharmingen, 555432), anti-human CD56-PE-Cy5
Tube 11: anti-human CD3-FITC, anti-human CD62L-PE (eBioscience, 12-0629-42), anti-human CD56-PE-Cy5
Tube 12: anti-human CD3-FITC, anti-human CD69-PE (R&D systems, FAB23591P), anti-human CD56-PE-Cy5
Tube 13: anti-human CD3-FITC, anti-human CXCR3-PE (BD Pharmingen, 557185), anti-human CD56-PE-Cy5
Tube 14: anti-human CD3-FITC, anti-human CD57-PE (BD Pharmingen, 560844), anti-human CD56-PE-Cy5
Tube 15: anti-human CD3-FITC, PE mouse IgG1 k isotype control (BD Pharmingen, 555749), anti-human CD56-PE-Cy5
Tube 16: FITC mouse IgG1 k isotype control (BD Pharmingen, 555748), PE mouse IgG1 k isotype control (BD Pharmingen, 555749), PE-Cy5 mouse IgG1 k isotype control (BD Pharmingen)

The tubes were stained at a cold temperature for 30 minutes, and the stained cells were added to 2 mL of FACS buffer and centrifuged at 1500 rpm for 5 minutes. The supernatant was removed, and the remaining cells were added again to 2 mL of FACS buffer and centrifuged at 1500 rpm for 5 minutes. Next, the supernatant was removed, and the remaining cells were suspended in 300 μL of FACS buffer, and the phenotypes thereof were analyzed using FACS LSRII Fortessa (Becton Dickinson), thereby determining the identity and purity of the cells. The content was expressed as the contents of CD3(−)CD56(+) cells and CD16(+)CD56(+) cells, and the purity was measured with CD3(+) for T cells, CD14(+) for monocytes, and CD19(+) for B cells.

4-1: Cell Identity and Purity

Figure 3A:
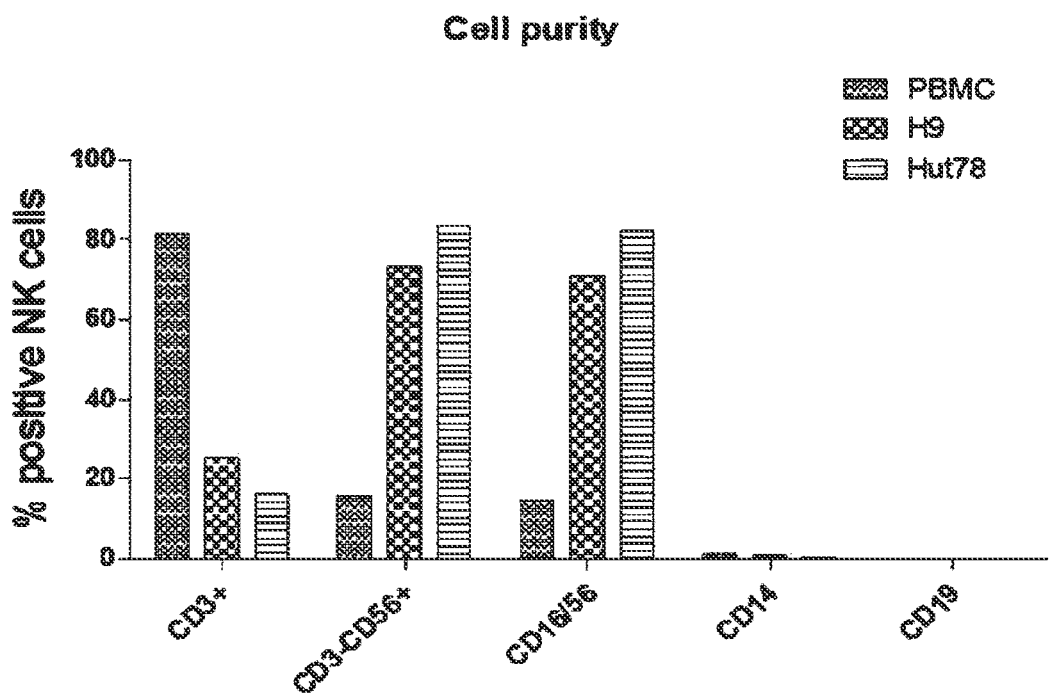
FIG. 3a shows the identity and purity of natural killer cells obtained by culturing PBMC seed cells using various T cells as feeder cells for 14 days (condition 1 in Table 1 below).
Figure 3B:
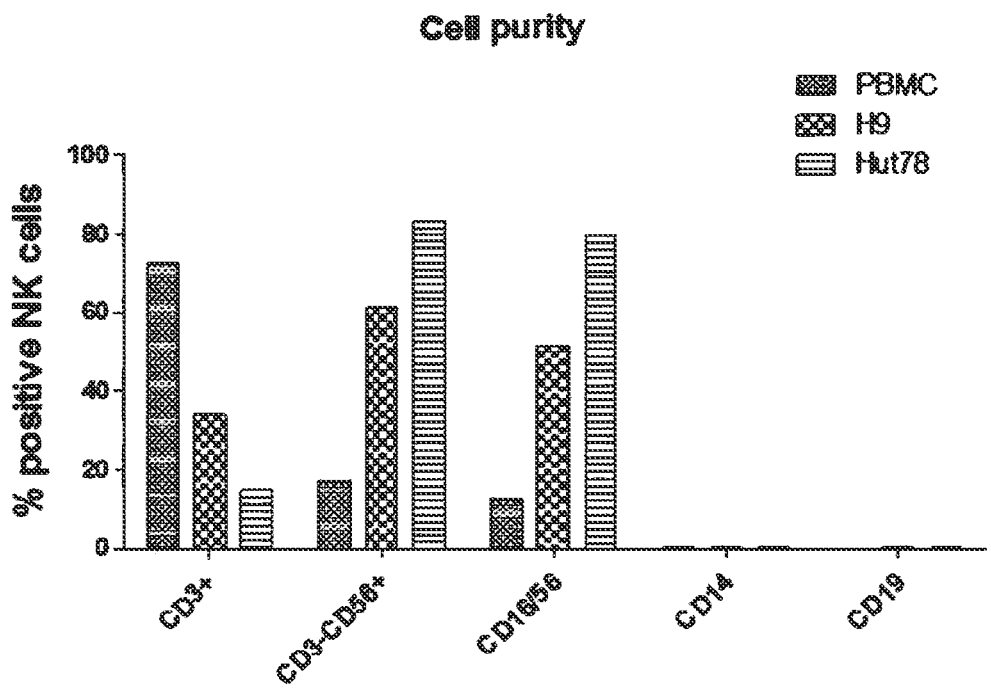
FIG. 3b shows the identity and purity of natural killer cells obtained by culturing PBMC seed cells using various T cells as feeder cells, and then re-stimulating the cells with various T cells serving as feeder cells, and culturing the cells up to day 21 (condition 2 in Table 1 below).

The identity and purity of natural killer cells cultured under conditions 1 and 2 shown in Table 1 were analyzed. As a result, the content of natural killer cells, evaluated after culturing PBMC seed cells with various feeder cells for 14 days, was 15.9% for PBMCs, 73.3% for H9, and 83.3% for HuT78, and the content of natural killer cells, evaluated after 21 days of culture, was 17.4% for PBMCs, 61.1% for H9, and 83.5% for HuT78 (see FIGS. 3a and 3b). Thus, it could be seen that, when PBMCs containing T cells were used as seed cells, in the case of PBMC feeder cells, T cells proliferated 80% or more, whereas in the case of H9 and HuT78, natural killer cells other than T cells selectively proliferated. Particularly, HuT78 showed a high natural killer cell content of 80% or more.

Figure 3C:
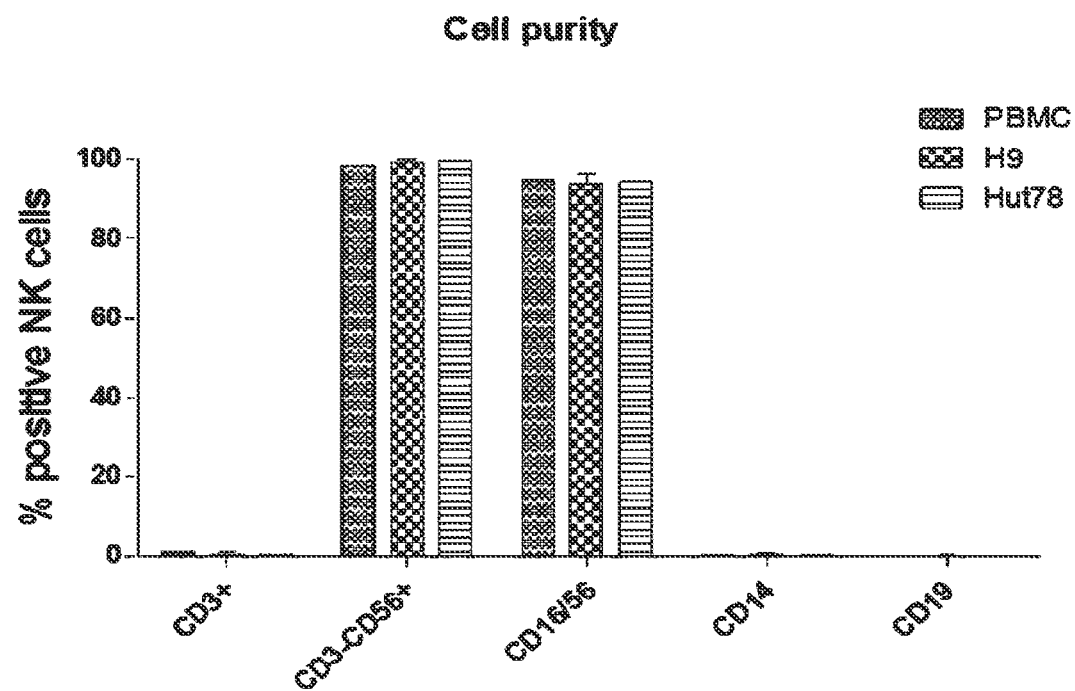
FIG. 3c shows the identity and purity of natural killer cells obtained by culturing CD3(+) cell-depleted PBMC seed cells using various T cells as feeder cells for 14 days (condition 3 in Table 1 below).
Figure 3D:
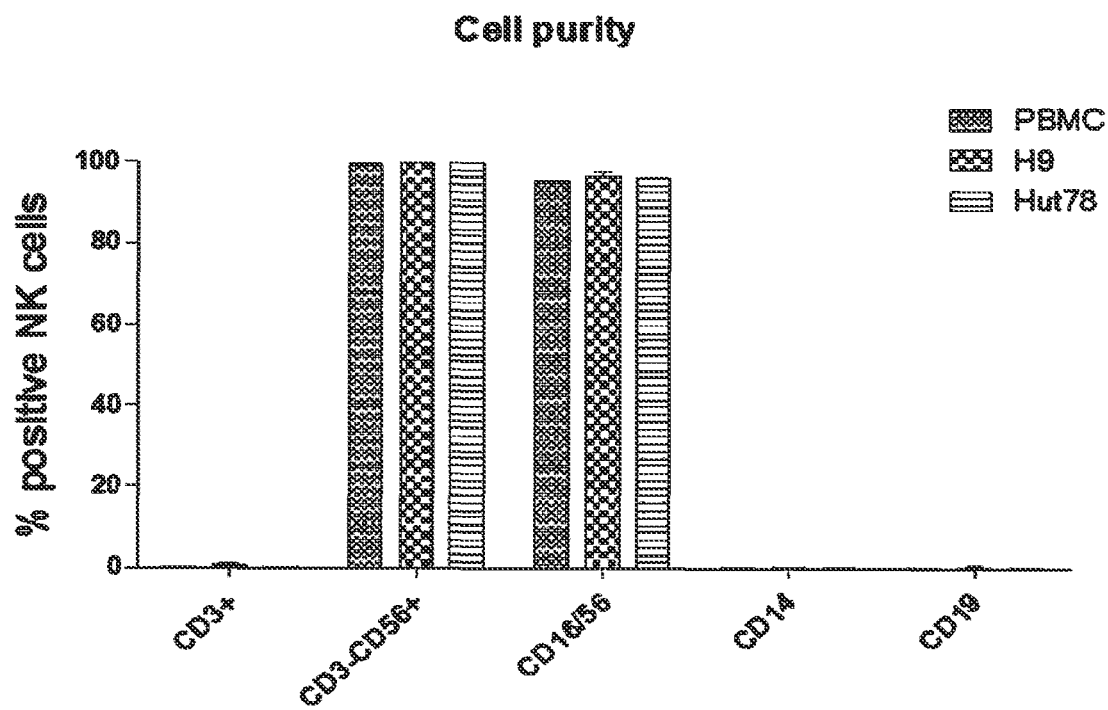
FIG. 3d shows the identity and purity of natural killer cells obtained by culturing CD3(+) cell-depleted PBMC seed cells using PBMC feeder cells, and then re-stimulating the cells with various T cells serving as feeder cells, and culturing the cells up to day 21 (condition 4 in Table 1 below).

The identity and purity of natural killer cells cultured under conditions 3 and 4 shown in Table 1 were analyzed. As a result, it was shown that, because T cell-depleted CD3(−) seed cells were used under both the conditions, all the types of feeder cells showed a high natural killer cell content of 95% or more, and the contents of T cells, monocytes and B cells were all measured to be 1% or less (FIGS. 3c and 3d).

Figure 3E:
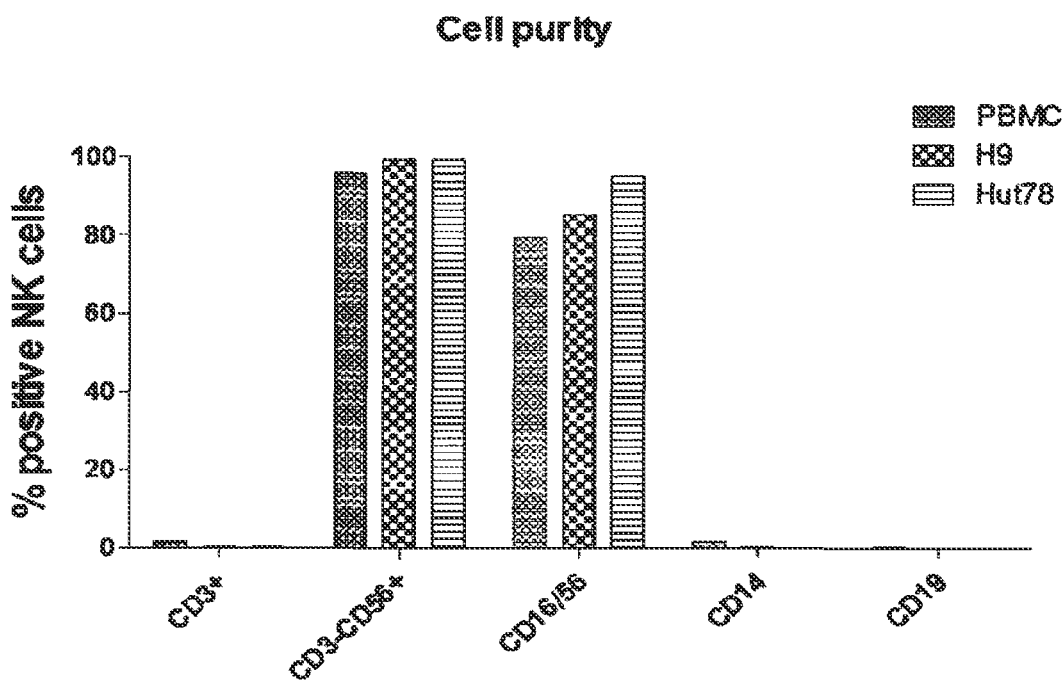
FIG. 3e shows the identity and purity of natural killer cells of poorly proliferating donors, obtained by culture under condition 3 of Table 1 below.

In addition, in the case of poorly proliferating donor cells cultured under condition 3 shown in Table 1, it was shown that culture with PBMC feeder cells showed a decrease in purity of about 4% and a decrease in CD16 expression of about 16%, compared to culture with HuT78 (FIG. 3e). Thus, it could be seen that CD4-expressing T cells could induce the selective proliferation of natural killer cells only and can significantly overcome the difference in culture of natural killer cells between donors.

4-2: Cell Expression Markers

In addition to the identity and purity of cells, the expression of typical natural killer cell receptors, which differs depending on the type of feeder cells, was analyzed.

Figure 4A:
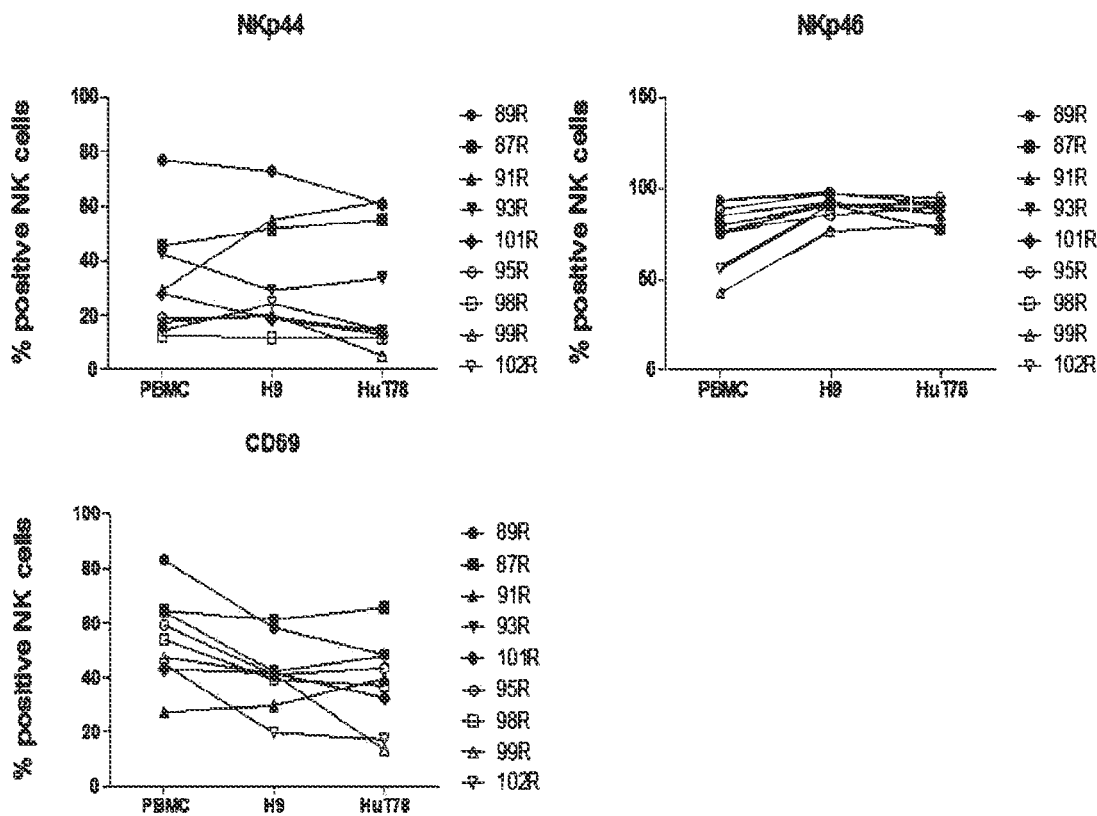
FIG. 4a shows an activation marker in natural killer cells obtained by culturing PBMC seed cells using various T cells as seed cells for 14 days (condition 1 in Table 1 below 1).

The cell phenotypes of natural killer cells cultured under condition 1 of Table 1 were analyzed. As a result, for NKp44, NKp46 and CD69, the difference in phenotype between culture conditions was observed (FIG. 4a).

Figure 4B:
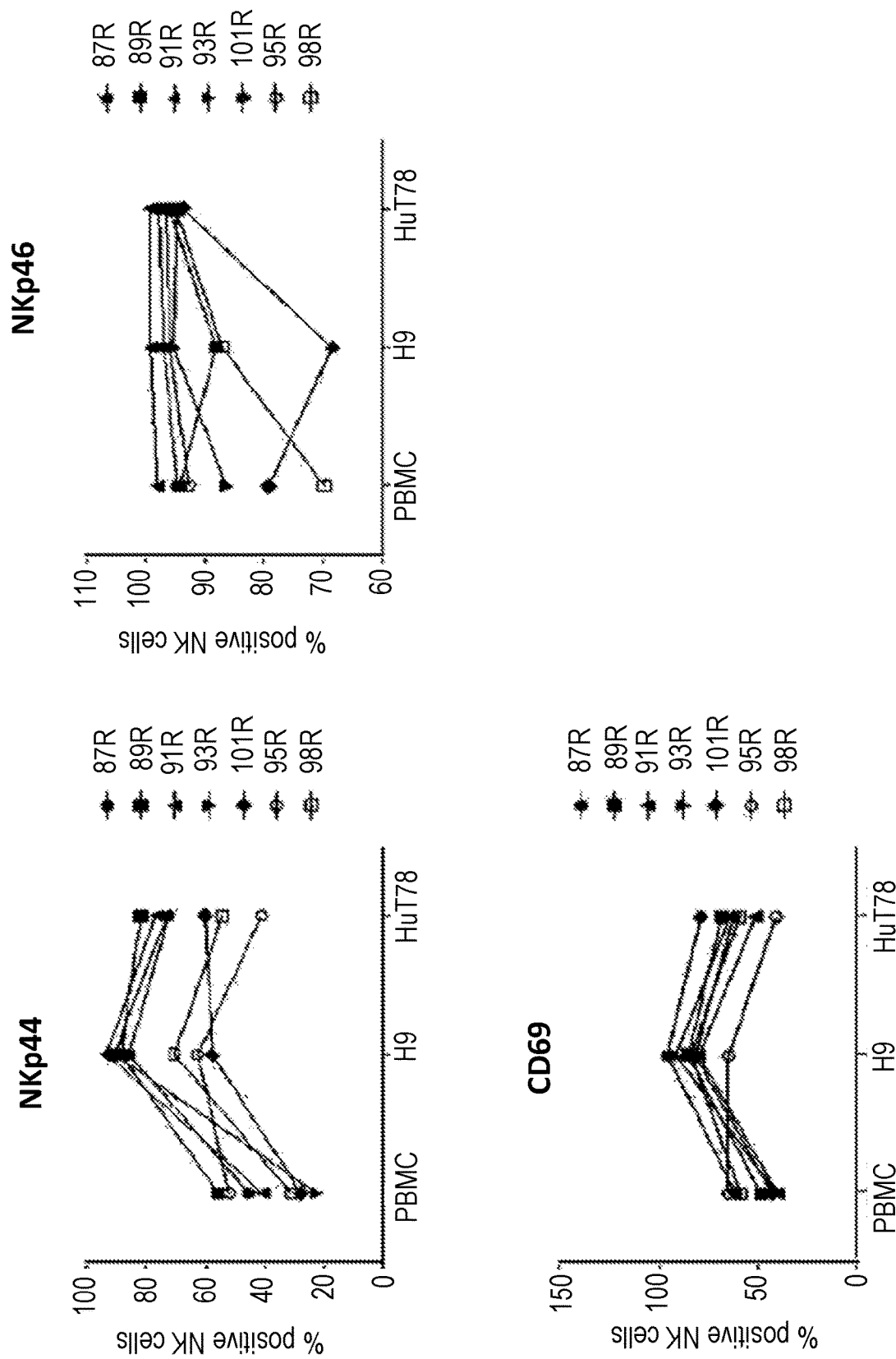
FIG. 4b shows an activation marker in natural killer cells obtained by CD3(+) cell-depleted PBMC seed cells using various T cells as feeder cells for 14 days (condition 3 in Table 1 below).

In addition, the cell phenotypes of natural killer cells cultured under condition 3 of Table 1 were analyzed. As a result, it was shown that the expression of NKp44 and NKp46 was higher in culture with H9 and HuT78 than in culture with PBMC and that the expression of CD69 was similar between culture with PBMC and culture with HuT78, but increased in culture with H9 (FIG. 4b).

Thus, it could be seen that, although the expression of cell phenotype markers did differ depending on the type of seed cells, the expression of natural killing cell activation markers such as NKp44 and NKp46 was significantly higher in culture with T feeder cells than in culture with PBMC feeder cells. These markers are important factors in the activity of natural killer cells, and the above results indicate that the efficacy of natural killer cells is higher in culture with T cells than in culture with PBMC feeder cells.

Example 5: In Vitro Cell Killing Activity Against Various Tumor Cell Lines $1 \times 10^6$ cells of each of target tumor cell lines (K562, HuT78, HuH-7, etc.) were dispensed into each of 15 mL tubes and centrifuged. Then, the cell pellets were suspended in 1 mL of RPMI 1640-10% FBS medium, after which 30 μL of 1 mM Calcein-AM (Molecular probe, C34852) was added thereto, and then the cells were stained in an incubator at 37° C. for 1 hour while light was blocked with silver paper. The tumor cell line stained with Calcein-AM was washed with 10-15 mL of RPMI 1640-10% FBS medium and centrifuged, and the pellets were suspended in 10 mL of RPMI medium to a concentration of $1 \times 10^5$ cells/mL.

$3 \times 10^6$ natural killer cells were dispensed into each of 15 mL tubes and centrifuged, and the pellets were suspended in RPMI 1640-10% FBS medium at a desired ratio relative to the target tumor cell line. 100 μL of each of the prepared target tumor cell line and natural killer cell line was dispensed into each well of a round-bottom 96-well plate, and each well was prepared in triplicate. To each spontaneous release well, 100 μL of the stained tumor cell line and 100 μL of RPMI 1640-10% FBS medium were added. To each maximum release well, 100 μL of the stained tumor cell line and 100 μL of 2% Triton-X 100 solution were added. To correct an autofluorescence value present in RPMI 1640-10% FBS medium and 2% Triton-X 100 solution, 200 μL of RPMI 1640-10% FBS medium was added to prepare a medium value, 100 μL of 2% Triton-X 100 solution was added to 100 μL of RPMI 1640-10% FBS medium to prepare the value of the mixture of the two solutions. The difference (A) obtained by subtracting the value of the mixture from the medium value was added to the maximum release value, thereby correcting the autofluorescence value.

The cells were incubated in an incubator at 37° C. for 4 hours under a light-shielding condition, and then the plate was centrifuged at 2000 rpm for 3 minutes. 100 μL of the supernatant was added to each well of a 96-well black plate, and the fluorescence value ($OD_{480/535\ nm}$) was measured using a fluorescence plate reader (Perkin Elmer, VICTOR X3). Based on the measured fluorescence value, the tumor cell killing activity of the natural killer cells was calculated using the following equation:

% of killing=(Average fluorescence value of sample wells—average fluorescence value of spontaneous wells)/{(average fluorescence value of maximum wells+A)—average fluorescence value of spontaneous wells}×100

Natural killer cells cultured with various feeder cells were allowed to react with various tumor cell lines, and the direct tumor cell killing activity of the natural killer cells was measured.

Figure 5A:
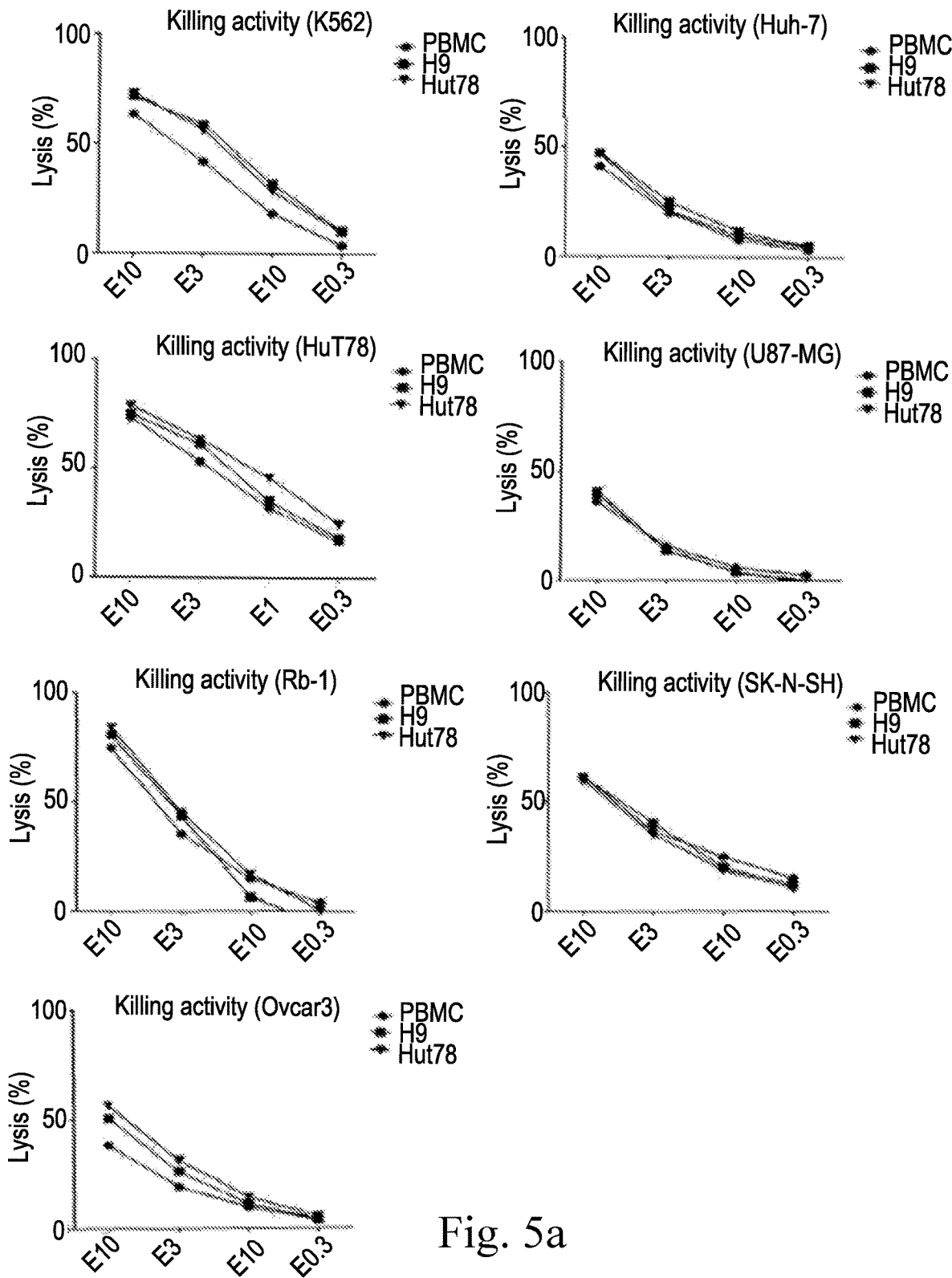
FIG. 5a shows the cell killing activities against various cancers of natural killer cells obtained by culturing PBMC seed cells using various T cells as feeder cells for 14 days (condition 1 in Table 1 below).

The cell killing activity of natural killer cells cultured under condition 1 (14-day culture of PBMC seed cells with various feeder cells) shown in Table 1 was evaluated against the blood cancer cell line K562, the liver cancer cell line HuH-7, the lymphoma cell line HuT78, the brain tumor cell line U87-MG, the retinoblastoma cell line SNUOT-Rbl, the neuroblastoma cell line SK-N-SH and the ovarian cancer cell line OVCAR-3. As a result, it was shown that culture with PBMC feeder cells showed a higher cell killing activity against all the tumor targets compared with culture with H9 and HuT78 (FIG. 5a).

Figure 5B:
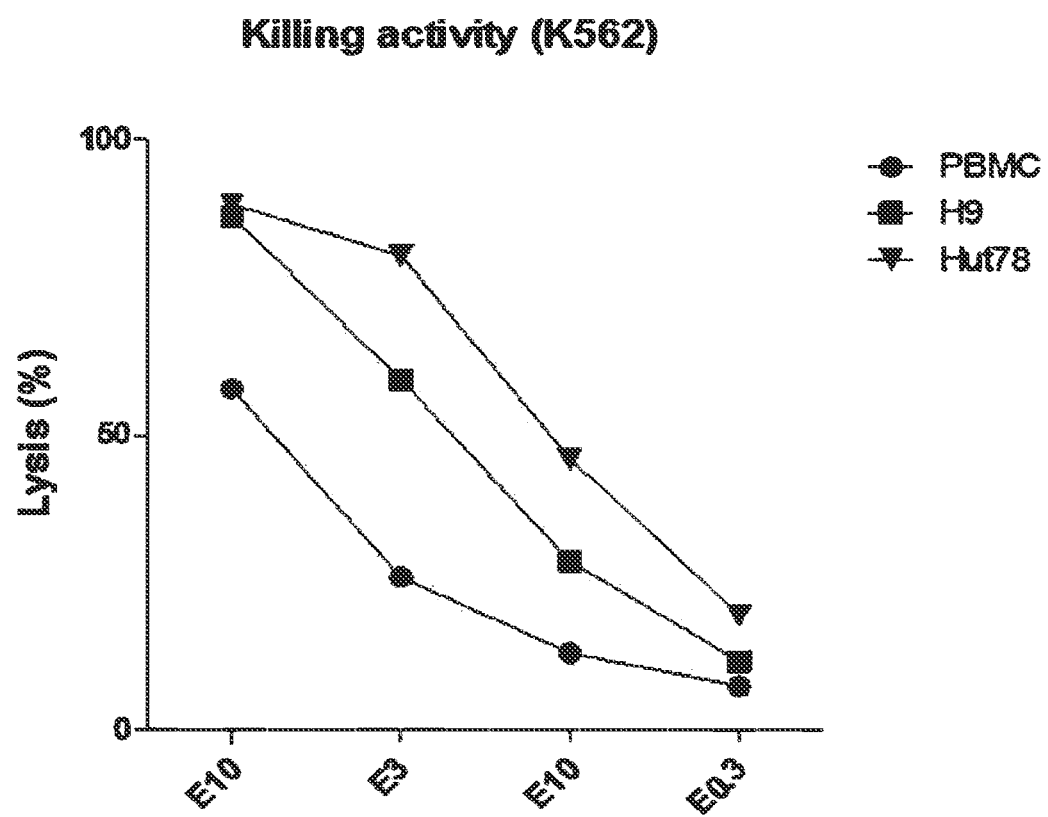
FIG. 5b shows the cell killing activities against various cancers of natural killer cells obtained by culturing PBMC seed cells using various T cells as feeder cells, and then re-stimulating the cells with various T cells serving as feeder cells, and culturing the cells up to day 21 (condition 2 in Table 1 below).

The cell killing activity of natural killer cells cultured under condition 2 (21-day culture of PBMC seed cells) shown in Table 1 was measured. As a result, it was shown that the cell killing activity against the K562 tumor cell line was higher in the order of HuT78>H9>PBMCs (FIG. 5b).

Figure 5C:
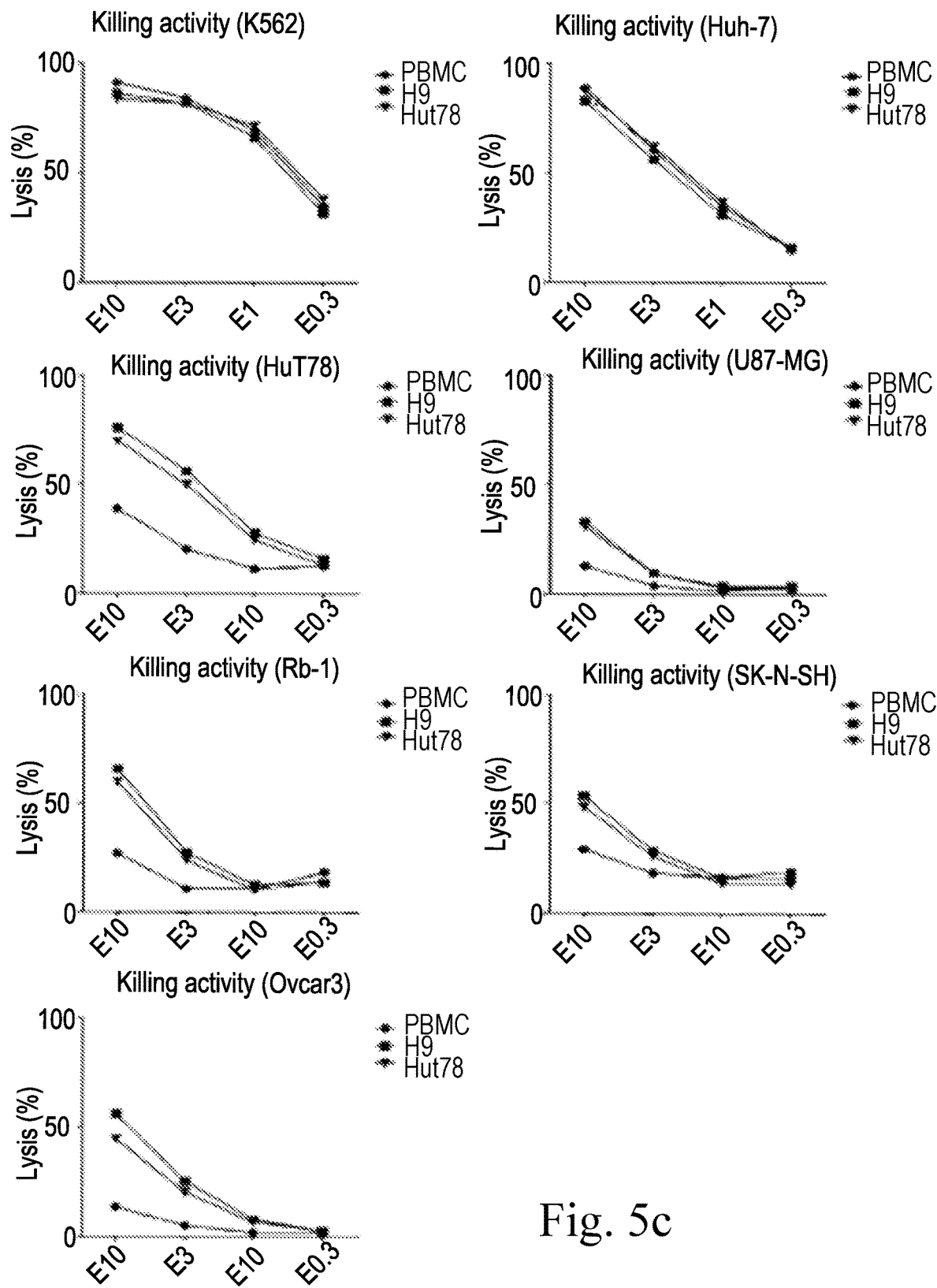
FIG. 5c shows the cell killing activities against various cancers of natural killer cells obtained by culturing CD3(+) cell-depleted PBMC seed cells using various T cells as feeder cells for 14 days (condition 3 in Table 1 below).

In addition, the cell killing activity of natural killer cells cultured under condition 3 (14-day culture of CD3(−) seed cells with various feeder cells) was evaluated against the blood cancer cell line K562, the liver cancer cell line HuH-7, the lymphoma cell line HuT78, the brain tumor cell line U87-MG, the retinoblastoma cell line SNUOT-Rbl, the neuroblastoma cell line SK-N-SH and the ovarian cancer cell line OVCAR-3. As a result, it was shown that culture with H9 and HuT78 showed a higher cell killing activity against most of the tumor targets (excluding K562) compared to culture with PBMC feeder cells, and particularly, this difference was more significant in the case of cancer cells having resistance to the killing activity of natural killer cells (FIG. 5c).

Figure 5D:
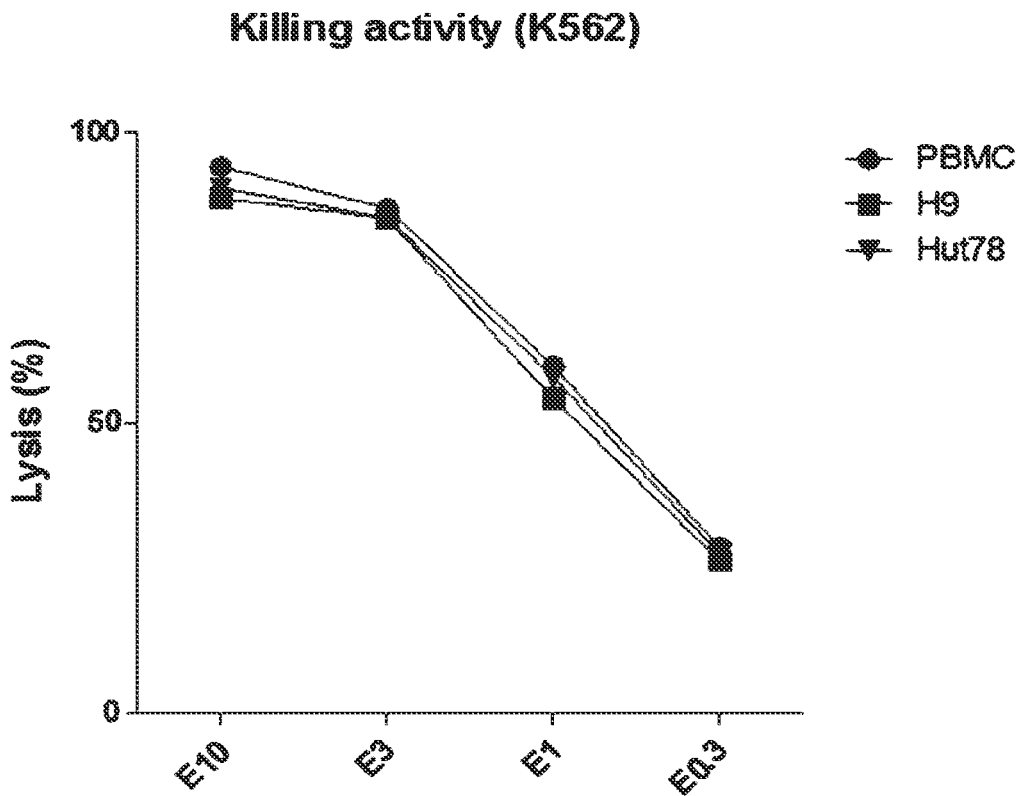
FIG. 5d shows the cell killing activities against various cancers of natural killer cells obtained by culturing CD3(+) cell-depleted PBMC seed cells using PBMC feeder cells, and then re-stimulating the cells with various T cells serving as feeder cells, and culturing the cells up to day 21 (condition 4 in Table 1 below).

The cell killing activity of natural killer cells cultured under condition 4 (21-day culture of CD3(−) seed cells) shown in Table 1 was measured. As a result, it was shown that the cell killing activity against the K562 tumor cell line was similar between the types of feeder cells (FIG. 5d). This insignificant difference in specificity between the types of feeder cells appears to be because PBMCs were used in the first stimulation of seed cells in the same manner and PBMCs and various T cells were used only in the second stimulation.

Figure 5E:
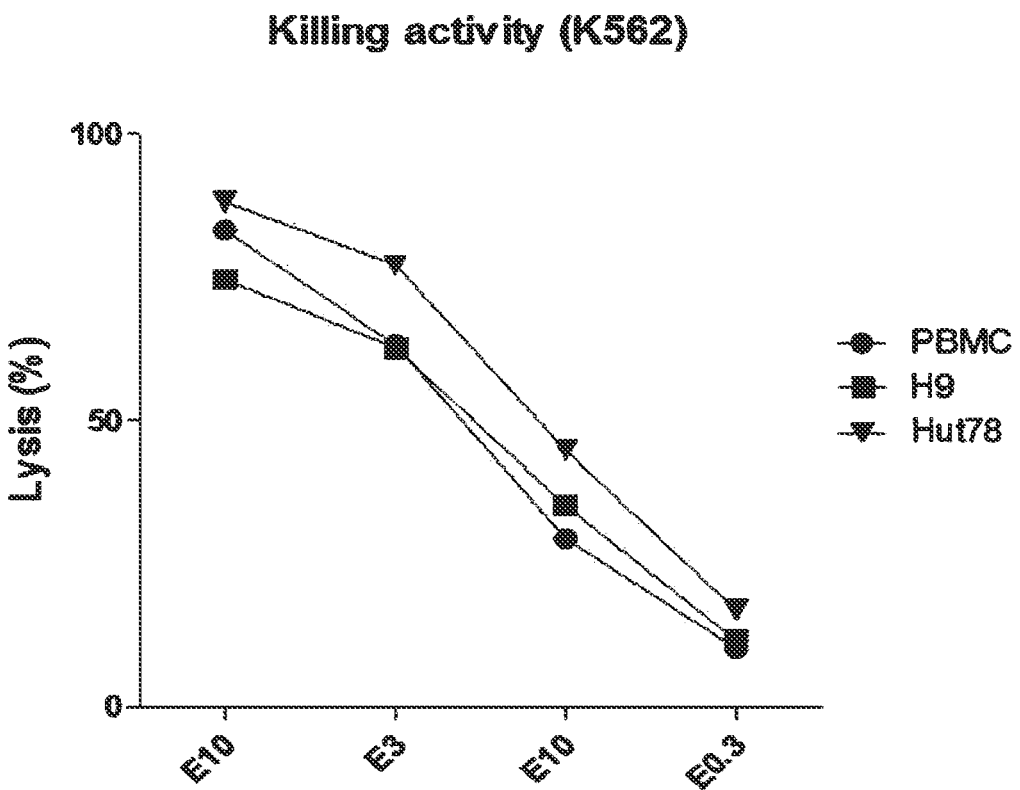
FIG. 5e shows the cell killing activities against K562 of natural killer cells of poorly proliferating donors, obtained by culture under condition 3 of Table 1 below.

The cell killing activity of natural killer cells in the case of poorly proliferating donor cells, cultured under condition 3 of Table 3, was measured. As a result, it was shown that HuT78 showed the highest killing activity against the K562 tumor cell line and that H9 and PBMC feeder cells showed similar killing activities (FIG. 5e).

In conclusion, HuT78 showed the highest cell killing activity against various tumor cell lines under most of the conditions. Particularly, natural killer cells cultured with H9 and HuT78 showed higher killing activities against tumor cell lines having resistance, indicating that H9 and HuT78 cells are feeder cells which are better than PBMCs in terms of efficacy.

The characteristics of natural killer cells cultured under conditions 1, 2, 3 and 4 are summarized in the following Tables 2 to 5.

TABLE 2

Characteristics of natural killer cells cultured under condition 1

|  | Expansion fold TNC | Expansion fold NK | Viability | % of CD3-CD56+ | % of Cytotoxidity against K562 ET ratio = 3:1 |
|---|---|---|---|---|---|
| PBMC | 147 (62) | 272 (180) | 77% (0) | 15.9% (12.5) | 41.5% (13.5) |
| H9 | 298 (108) | 2752 (386) | 83% (2) | 73.3% (7.0) | 58.7% (5.9) |
| HuT78 | 485 (31) | 5649 (2966) | 87% (1) | 83.3% (0.5) | 56.2% (3.9) |

Mean(SD)

TABLE 3

Characteristics of natural killer cells cultured under condition 2

|  | Expansion fold TNG | Expansion fold NK | Viability | % of CD3-CD56+ | % of Cytotoxidity against K562 ET ratio = 3:1 |
|---|---|---|---|---|---|
| PBMC | 334 (183) | 1257 (1498) | 76% (2) | 17.4% (9.1) | 26.0% (8.7) |
| H9 | 358 (60) | 2677 (268) | 72% (3) | 61.1% (12.9) | 59.4% (11.8) |
| HuT78 | 2282 (509) | 29455 (21088) | 87% (5) | 83.5% (2.8) | 80.3% (6.2) |

Mean(SD)

TABLE 4

Characteristics of natural killer cells cultured under condition 3

|  | Expansion fold TNG | Viability | % of CD3-CD56+ | of Cytotoxidity against K562 ET ratio = 3:1 |
|---|---|---|---|---|
| PBMC | 184 (81) | 92% (2) | 99.3% (0.4) | 84.2% (4.0) |
| H9 | 62 (24) | 90% (1) | 99.5% (0.4) | 81.9% (2.8) |
| HuT78 | 217 (1) | 91% (2) | 99.8% (1) | 81.9% (2.8) |

Mean(SD) %

TABLE 5

Characteristics of natural killer cells cultured under condition 4

|  | Expansion fold TNC | Viability | % of CD3-CD56+ | Mean (SD) % of Cytotoxidity against K562 ET ratio = 3:1 |
|---|---|---|---|---|
| PBMC | 1402 (506) | 91% (4) | 99.5% (0.3) | 87.0% (2.4) |
| H9 | 720 (288) | 88% (4) | 99.6% (0.3) | 85.2% (6.0) |
| HuT78 | 1393 (161) | 91% (5) | 99.8% (0.1) | 85.3% (4.1) |

INDUSTRIAL APPLICABILITY

As described above, the method for producing natural killer cells using T cells according to the present invention is a method capable of producing natural killer cells by selectively proliferating only natural killer cells from a small amount of seed cells while maintaining the high killing activity of the natural killer cells. The method of the present invention can produce a large amount of natural killer cells that can be frozen, and thus is useful for commercialization of cell therapeutic agents.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating cancer, the method comprising: administering to a subject in need thereof a therapeutically effective amount of a population of natural killer cells produced by the method comprising:
   (a) providing CD3(+)-depleted seed cells comprising mononuclear cells comprising natural killer cells;
   (b) expanding the natural killer cells by culturing the seed cells with a plurality of cells from an inactivated CD4(+) T cell line in a medium comprising:
      a T-cell stimulating antibody selected from the group consisting of OKT3, UCHT1, HTa, or a combination thereof; and
      IL-2,
   to produce expanded natural killer cells,
   thereby producing the population of natural killer cells.

2. The method of claim 1, wherein the seed cells provided in step (a) have not been expanded ex vivo or in vitro.

3. The method of claim 1, wherein the seed cells provided in step (a) are selected from peripheral blood cells, peripheral blood leukocytes, and PBMCs (peripheral blood mononuclear cells).

4. The method of claim 1, wherein the cells from an inactivated CD4(+) T cell line are selected from the group consisting of H9, HuT78, Molt-3, PEER, and combinations thereof.

5. The method of claim 4, wherein the cells from an inactivated CD4(+) T cell line are selected from the group consisting of H9, HuT78, and combinations thereof.

6. The method of claim 1, wherein the culturing is carried out for 5-60 days.

7. The method of claim 1, further comprising:
   (c) culturing the expanded natural killer cell(s) produced in step (b) with a second plurality of cells from an inactivated CD4(+) T cell line.

8. The method of claim 1, wherein the population of natural killer cells is administered as part of a pharmaceutical composition further comprising a pharmaceutically acceptable carrier.

9. The method of claim 1, wherein the cancer is selected from blood cancer, lymphoma, liver cancer, brain cancer, retinoblastoma, neuroblastoma, and ovarian cancer.

10. The method of claim 7, wherein the second plurality of cells from an inactivated CD4(+) T cell line are selected from the group consisting of H9, HuT78, Molt-3, PEER, and combinations thereof.

11. The method of claim 7, wherein the second plurality of cells from an inactivated CD4(+) T cell line are selected from the group consisting of H9, HuT78, and combinations thereof.

12. The method of claim 5, wherein the seed cells provided in step (a) have not been expanded ex vivo or in vitro.

13. The method of claim 12, wherein the population of natural killer cells is administered as part of a pharmaceutical composition further comprising a pharmaceutically acceptable carrier.

14. The method of claim 13, wherein the cancer is selected from blood cancer, lymphoma, liver cancer, brain cancer, retinoblastoma, neuroblastoma, and ovarian cancer.

* * * * *